(12) United States Patent
Gonzalez et al.

(10) Patent No.: US 11,540,945 B2
(45) Date of Patent: Jan. 3, 2023

(54) OPTICAL SURFACE IDENTIFICATION FOR LASER EYE SURGERY

(71) Applicant: AMO DEVELOPMENT, LLC, Irvine, CA (US)

(72) Inventors: Javier G. Gonzalez, Palo Alto, CA (US); Bruce Woodley, Palo Alto, CA (US)

(73) Assignee: AMO Development, LLC, Irvine, CA (US)

( * ) Notice: Subject to any disclaimer, the term of this patent is extended or adjusted under 35 U.S.C. 154(b) by 613 days.

(21) Appl. No.: 16/601,478

(22) Filed: Oct. 14, 2019

(65) Prior Publication Data

US 2020/0038244 A1 Feb. 6, 2020

Related U.S. Application Data

(60) Division of application No. 15/376,491, filed on Dec. 12, 2016, now Pat. No. 10,441,464, which is a (Continued)

(51) Int. Cl.
*A61F 9/008* (2006.01)
*A61B 3/10* (2006.01)
(Continued)

(52) U.S. Cl.
CPC .......... *A61F 9/00825* (2013.01); *A61B 3/102* (2013.01); *A61B 3/107* (2013.01);
(Continued)

(58) Field of Classification Search
CPC ......... A61B 3/102; A61B 3/107; A61B 3/117; A61B 5/0066; A61F 9/008;
(Continued)

(56) References Cited

U.S. PATENT DOCUMENTS 5,459,570 A 10/1995 Swanson et al.
5,720,894 A 2/1998 Neev et al.
(Continued)

FOREIGN PATENT DOCUMENTS

EP 0697611 A2 2/1996
WO 2011091326 A1 7/2011
(Continued)

OTHER PUBLICATIONS

Fercher A.F., et al., "Complex Spectral Interferometry OCT," Proceedings of the SPIE, 1999, vol. 3564, pp. 173-178.
(Continued)

*Primary Examiner* — Jack Dinh
(74) *Attorney, Agent, or Firm* — Johnson & Johnson Surgical Vision, Inc.

(57) ABSTRACT

Systems and methods automatically locate optical surfaces of an eye and automatically generate surface models of the optical surfaces. A method includes OCT scanning of an eye. Returning portions of a sample beam are processed to locate a point on the optical surface and first locations on the optical surface within a first radial distance of the point. A first surface model of the optical surface is generated based on the location of the point and the first locations. Returning portions of the sample beam are processed so as to detect second locations on the optical surface beyond the first radial distance and within a second radial distance from the point. A second surface model of the optical surface is generated based on the location of the point on the optical surface and the first and second locations on the optical surface.

10 Claims, 29 Drawing Sheets

Related U.S. Application Data continuation of application No. 14/070,245, filed on Nov. 1, 2013, now Pat. No. 9,549,670.

(60) Provisional application No. 61/722,080, filed on Nov. 2, 2012.

(51) Int. Cl.
| | |
|---|---|
| A61B 3/107 | (2006.01) |
| A61B 3/117 | (2006.01) |
| A61B 5/00 | (2006.01) |
| A61F 9/009 | (2006.01) |

(52) U.S. Cl.
CPC .............. *A61B 3/117* (2013.01); *A61F 9/008* (2013.01); *A61B 5/0066* (2013.01); *A61F 9/009* (2013.01); *A61F 2009/00851* (2013.01); *A61F 2009/00882* (2013.01); *A61F 2009/00887* (2013.01)

(58) Field of Classification Search
CPC ................. A61F 9/00825; A61F 9/009; A61F 2009/00851; A61F 2009/00882; A61F 2009/00887

See application file for complete search history.

(56) References Cited

U.S. PATENT DOCUMENTS

| | | | |
|---|---|---|---|
| 5,748,352 A | 5/1998 | Hattori | |
| 5,748,898 A | 5/1998 | Ueda | |
| 5,957,915 A | 9/1999 | Trost | |
| 5,984,916 A | 11/1999 | Lai | |
| 6,019,472 A | 2/2000 | Koester et al. | |
| 6,053,613 A | 4/2000 | Wei et al. | |
| 6,111,645 A | 8/2000 | Tearney et al. | |
| 6,454,761 B1 | 9/2002 | Freedman | |
| 7,649,629 B2 | 1/2010 | Rogers et al. | |
| 7,655,002 B2 | 2/2010 | Myers et al. | |
| 7,717,907 B2 | 5/2010 | Ruiz et al. | |
| 7,954,948 B2 | 6/2011 | Nozato et al. | |
| 8,262,646 B2 | 9/2012 | Frey et al. | |
| 8,350,183 B2 | 1/2013 | Vogel et al. | |
| 8,376,547 B2 | 2/2013 | Hirose | |
| 8,382,745 B2 | 2/2013 | Naranjo-Tackman et al. | |
| 8,414,564 B2 | 4/2013 | Goldshleger et al. | |
| 8,625,104 B2 | 1/2014 | Izatt et al. | |
| 8,783,866 B2 | 7/2014 | Hart et al. | |
| 8,820,931 B2 | 9/2014 | Walsh et al. | |
| 8,845,625 B2 | 9/2014 | Angeley et al. | |
| 9,050,027 B2 | 6/2015 | Uhlhorn et al. | |
| 9,119,571 B2 | 9/2015 | Kato et al. | |
| 9,125,593 B2 | 9/2015 | Isogai et al. | |
| 9,259,150 B2 | 2/2016 | Izatt et al. | |
| 9,445,946 B2 | 9/2016 | Angeley et al. | |
| 9,492,079 B2 | 11/2016 | Walsh et al. | |
| 9,492,080 B2 | 11/2016 | Uhlhorn et al. | |
| 9,492,322 B2 | 11/2016 | Goldshleger et al. | |
| 9,495,743 B2 | 11/2016 | Angeley et al. | |
| 9,549,670 B2 | 1/2017 | Gonzalez et al. | |
| 9,622,658 B2 | 4/2017 | Hart et al. | |
| 9,649,024 B2 | 5/2017 | Hacker et al. | |
| 9,681,803 B2 | 6/2017 | Isogai et al. | |
| 9,721,351 B2 | 8/2017 | Gonzalez et al. | |
| 9,814,383 B2 | 11/2017 | Hart et al. | |
| 9,867,536 B2 | 1/2018 | Izatt et al. | |
| 9,918,873 B2 | 3/2018 | Woodley et al. | |
| 9,996,938 B2 | 6/2018 | Gonzalez et al. | |
| 9,999,349 B2 | 6/2018 | Kato et al. | |
| 2009/0182310 A1 | 7/2009 | Gertner et al. | |
| 2009/0268161 A1 | 10/2009 | Hart et al. | |
| 2011/0102740 A1 | 5/2011 | Hirose | |
| 2011/0102802 A1 | 5/2011 | Izatt et al. | |
| 2011/0118609 A1 | 5/2011 | Goldshleger et al. | |
| 2011/0202046 A1 | 8/2011 | Angeley et al. | |
| 2011/0299034 A1 | 12/2011 | Walsh et al. | |
| 2011/0319873 A1 | 12/2011 | Raksi et al. | |
| 2011/0319875 A1 | 12/2011 | Loesel et al. | |
| 2012/0140173 A1 | 6/2012 | Uhlhorn et al. | |
| 2014/0114296 A1 | 4/2014 | Woodley et al. | |
| 2014/0114297 A1 | 4/2014 | Woodley et al. | |
| 2014/0128852 A1 | 5/2014 | Gooding et al. | |
| 2014/0128853 A1 | 5/2014 | Angeley et al. | |
| 2014/0343541 A1 | 11/2014 | Scott et al. | |
| 2015/0018674 A1 | 1/2015 | Scott et al. | |
| 2016/0095752 A1 | 4/2016 | Srinivasan et al. | |
| 2016/0106581 A1 | 4/2016 | Gonzalez et al. | |
| 2016/0106588 A1 | 4/2016 | Srinivasan et al. | |
| 2016/0228296 A1 | 8/2016 | Woodley et al. | |
| 2017/0007112 A1 | 1/2017 | Gonzalez | |
| 2017/0027756 A1 | 2/2017 | Angeley et al. | |
| 2017/0119247 A1 | 5/2017 | Walsh et al. | |
| 2017/0189233 A1 | 7/2017 | Dewey et al. | |
| 2018/0207031 A1 | 7/2018 | Woodley et al. | |

FOREIGN PATENT DOCUMENTS

| | | |
|---|---|---|
| WO | 2012027849 A1 | 3/2012 |
| WO | 2013059719 A2 | 4/2013 |

OTHER PUBLICATIONS

Gotzinger E., et al., "High Speed Full Range Complex Spectral Domain Optical Coherence Tomography," Optics Express, Jan. 24, 2005, vol. 13 (2), pp. 583-594.

International Search Report and Written Opinion for Application No. PCT/US2013/068120, dated May 16, 2014, 19 pages.

Targowski P., et al., "Complex Spectral OCT in Human Eye Imaging in vivo," Optics Communications, 2004, vol. 229 (1-6), pp. 79-84.

Wojtkowski M., et al., "Full Range Complex Spectral Optical Coherence Tomography Technique in Eye Imaging," Optics Letters, 2002, vol. 27 (16), pp. 1415-1417.

Yaqoob Z., et al., "Spectral Domain Optical Coherence Tomography: A Better Oct Imaging Strategy," Journal of BioTechniques, 2005, vol. 39 (6 Suppl), pp. S6-S13.

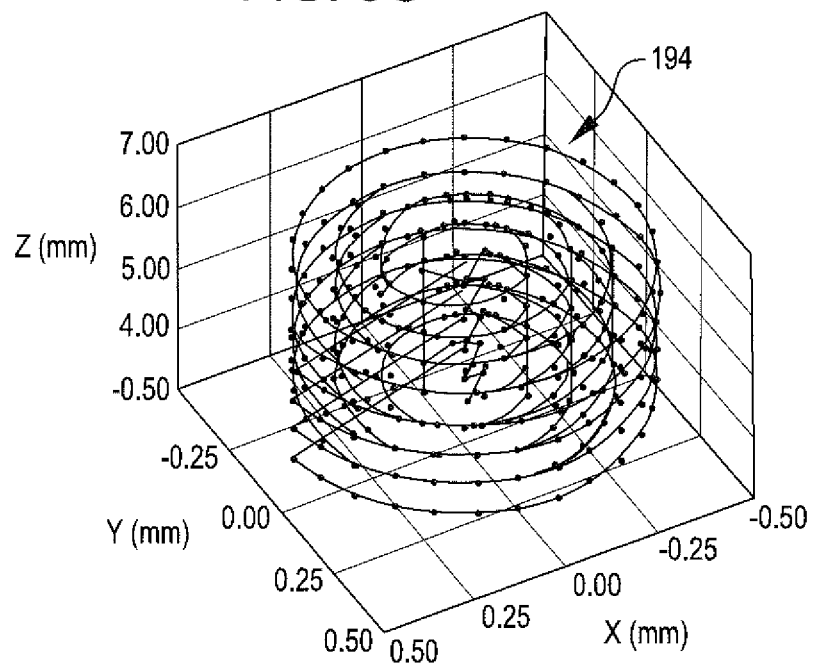

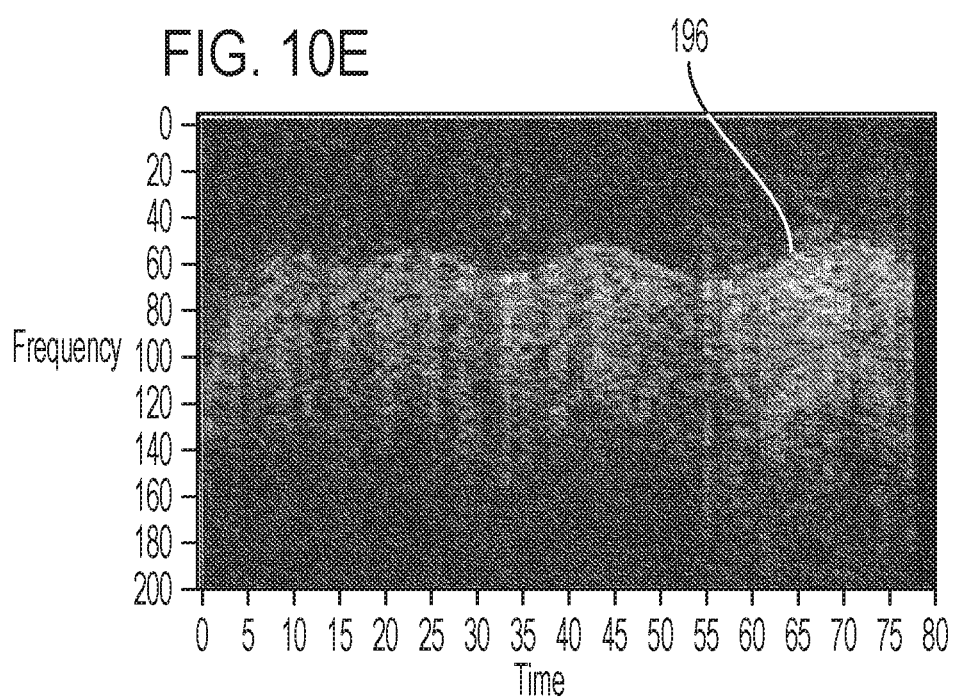

OPTICAL SURFACE IDENTIFICATION FOR LASER EYE SURGERY

CROSS REFERENCE TO RELATED APPLICATIONS

This application is a divisional of and claims priority to U.S. application Ser. No. 15/376,491, filed Dec. 12, 2016, which is a continuation of and claims priority to U.S. application Ser. No. 14/070,245, filed on Nov. 1, 2013, which claims the benefit of priority to U.S. Provisional Application No. 61/722,080, filed Nov. 2, 2012, all of which are herein incorporated by reference in their entirety.

BACKGROUND

Cataract extraction is one of the most commonly performed surgical procedures in the world. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye. Typically, the IOL is held in place by the edges of the anterior capsule and the capsular bag. The IOL may also be held by the posterior capsule, either alone or in unison with the anterior capsule. This latter configuration is known in the field as a "Bag-in-Lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the anterior lens capsule in a circular fashion followed by the removal of a circular fragment of lens capsule typically in the range of 5-8 mm in diameter. The smaller the capsulotomy, the more difficult it is to produce manually. The capsulotomy provides access for the next step of nuclear sculpting by phacoemulsification. Due to a variety of complications associated with the initial can-opener technique, attempts were made by leading experts in the field to develop a better technique for removal of the circular fragment of the anterior lens capsule prior to the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the anterior lens capsule provides access for tool insertion during removal of the nucleus and for IOL insertion, a permanent aperture for transmission of the image to the retina of the patient, and also support of the IOL inside the remaining lens capsule that limits the potential for dislocation. The resulting reliance on the shape, symmetry, uniformity, and strength of the remaining lens capsule to contain, constrain, position, and maintain the IOL in the patient's eye limits the placement accuracy of the IOL, both initially and over time. Subsequently, a patient's refractive outcome and resultant visual acuity are less deterministic and intrinsically sub-optimal due to the IOL placement uncertainty. This is especially true for astigmatism correcting ("toric") and accommodating ("presbyopic") IOLs.

Problems may also develop related to inability of the surgeon to adequately visualize the lens capsule due to lack of red reflex, to grasp the lens capsule with sufficient security, and to tear a smooth circular opening in the lens capsule of the appropriate size and in the correct location without creating radial rips and extensions. Also present are technical difficulties related to maintenance of the depth of the anterior chamber depth after opening the lens capsule, small pupils, or the absence of a red reflex due to the lens opacity. Some of the problems with visualization can be minimized through the use of dyes such as methylene blue or indocyanine green. Additional complications may also arise in patients with weak zonules (typically older patients) and very young children that have very soft and elastic lens capsules, which are very difficult to controllably and reliably rupture and tear.

The implantation of a "Bag-in-Lens" IOL typically uses anterior and posterior openings in the lens capsule of the same size. Manually creating matching anterior and posterior capsulotomies for the "Bag-in-Lens" configuration, however, is particularly difficult.

Many cataract patients have astigmatic visual errors. Astigmatism can occur when the corneal curvature is unequal in all directions. An IOL can be used to correct for astigmatism but require precise rotational and central placement. Additionally, IOLs are not typically used for correction beyond 5D of astigmatism. Many patients, however, have astigmatic visual errors exceeding 5D. Higher correction beyond 5D typically requires reshaping the cornea to make it more spherical. There are numerous existing approaches for reshaping the cornea, including Corneaplasty, Astigmatic Keratotomy, Corneal Relaxing Incision (CRI), and Limbal Relaxing Incision (LRI). In Astigmatic Keratotomy, Corneal Relaxing Incision (CRI), and Limbal Relaxing Incision (LRI), corneal incisions are made in a well-defined manner and depth to allow the cornea to change shape to become more spherical. Presently, these corneal incisions are typically accomplished manually often with limited precision.

Thus, improved methods and systems for treating cataracts and/or creating corneal incisions are needed.

SUMMARY

Methods and systems related to laser eye surgery are disclosed. A laser can be used to form precise incisions in the cornea, in the lens capsule, and/or in the crystalline lens nucleus. Structures of an eye, such as the cornea, the lens, the limbus, and the pupil can be measured via an efficient non-invasive scanning approach. Surface/curve models for the measured structures (e.g., cornea anterior surface, cornea posterior surface, lens anterior surface, lens posterior surface, iris, and limbus) can be automatically generated. The surface/curve models can be checked relative to suitable values and/or value ranges. Composite images of the surface/curve models and the respective structure can be displayed to, for example, enable user verification of the accuracy of the surface/curve model relative to the corresponding structure of the eye. The methods and system disclosed thus provide for fast and efficient planning and control of laser eye surgery procedures that can include precise incisions in the cornea, in the lens capsule, and/or in the crystalline lens nucleus.

Thus, in one aspect, a method is provided of identifying optical surfaces in a patient's eye for performing laser surgery on the patient's eye. The eye includes a cornea having an anterior surface and a lens capsule having an anterior portion and a posterior portion. The method includes coupling the patient's eye to a laser eye surgery system that includes an optical coherence tomography (OCT) imaging subsystem. The OCT imaging subsystem includes a reference path length that is adjustable so that a distance from the laser eye surgery system to a real portion detection window of the OCT imaging subsystem is adjustable. The OCT imaging subsystem employs a detection beam having a plurality of wavelengths such that the real portion detection window spans a range of distances relative to the laser eye surgery system. An OCT sample beam is generated. The OCT sample beam is focused at a plurality of different locations within the patient's eye. The plurality of different locations include at least two different distances from the laser eye surgery system. The different distances define a depth range encompassing an expected variability of distance from the laser eye surgery system to the corneal anterior surface, to the lens capsule anterior portion, or to the lens capsule posterior portion. Returning portions of the sample beam focused at the plurality of different locations are processed to locate, relative to the laser eye surgery system, the corneal anterior surface, the lens capsule anterior portion, or the lens capsule posterior portion.

Variations of the method of identifying optical surfaces in a patient's eye for performing laser surgery on the patient's eye are provided. For example, the different locations can be positioned at least three different distances from the laser eye surgery system. The different locations can be located at least four different distances from the laser eye surgery system. The different locations can be positioned at least five different distances from the laser eye surgery system. The five different distances can define four intervening separating distances of between 0.25 mm and 0.75 mm. At least one of the four intervening separating distances can be between 0.4 mm and 0.6 mm. The focusing of the OCT sample beam at a plurality of different locations within the patient's eye can include scanning the OCT sample beam in a pattern having a maximum transverse dimension of less than 2.0 mm for at least two of the different distances. The pattern can have a maximum dimension of less than 1.2 mm for at least two of the different distances. The reference path length can be held constant during the focusing of the OCT sample beam at a plurality of different locations within the patient's eye. A boundary surface within the detection window can divide the detection window into a real portion of the detection window and an imaginary portion of the detection window. The detection window imaginary portion can be disposed between the laser eye surgery system and the detection window real portion. Alternatively, the detection window real portion can be disposed between the laser eye surgery system and the detection window imaginary portion. The laser eye surgery system can be configured to employ an interface lens assembly that is removably mounted to the laser eye surgery system so as to be disposed between the OCT imaging subsystem and the eye. The interface lens assembly can include an interface lens having an anterior surface and a posterior surface. The method can include setting the reference path length to position the detection window boundary surface between the interface lens posterior surface and the corneal anterior surface such that the interface lens posterior surface is closer to the detection window boundary surface than the corneal anterior surface when processing returning portions of the sample beam focused at the plurality of different locations to locate the corneal anterior surface. The method can include setting the reference path length to position the detection window boundary surface between the interface lens posterior surface and the lens capsule anterior surface such that the interface lens posterior surface is further from the detection window boundary surface than the lens capsule anterior surface when processing returning portions of the sample beam focused at the plurality of different locations to locate the lens capsule anterior surface. The detection window boundary surface can be positioned such that the cornea anterior surface is closer to the detection window boundary surface than the lens capsule anterior surface when processing returning portions of the sample beam focused at the plurality of different locations to locate the lens capsule anterior surface. The method can include setting the reference path length to position the lens capsule posterior surface between the detection window boundary surface and the lens capsule anterior surface when processing returning portions of the sample beam focused at the plurality of different locations to locate the lens capsule posterior surface. The method can include using the OCT imaging system to locate the interface lens posterior surface. The method can include using the OCT imaging system to locate the interface lens anterior surface. The laser eye surgery system can be configured to employ an interface assembly that is removably mounted to the laser eye surgery system so as to be disposed between the OCT imaging subsystem and the eye. The interface assembly can include two or more reference features. The method can include using the OCT imaging subsystem to locate the reference features relative to the laser eye surgery system; and comparing the OCT based locations of the reference features relative to predetermined positions of the reference features to determine at least one of that the interface assembly is properly mounted to the laser eye surgery system, that the interface assembly is improperly mounted to the laser eye surgery system, that fluid is present in the interface assembly, that fluid is missing from the interface assembly, an angular orientation of the interface assembly relative to the laser eye surgery system, or whether the interface assembly is coupled with a left or a right eye of a patient. The interface assembly can include a suction ring assembly that is configured to be coupled with the eye and includes the two or more reference features and an interface lens assembly that includes an interface lens and couples the suction ring assembly to the laser eye surgery system.

In another aspect, a method is provided for processing optical coherence tomography (OCT) data to generate a surface model of an optical surface of a patient's eye. The patient's eye has a cornea having an anterior surface and a lens capsule having an anterior portion and a posterior portion. The method includes coupling the patient's eye to a laser eye surgery system that includes optical coherence tomography (OCT) imaging subsystem. The OCT imaging subsystem includes a reference path length that is adjustable so that a distance from the laser eye surgery system to a real portion detection window of the OCT imaging subsystem is adjustable. The OCT imaging subsystem employs a detection beam having a plurality of wavelengths such that the real portion detection window spans a range of distances relative to the laser eye surgery system. An OCT sample beam is generated. Returning portions of the sample beam are processed to locate a point on the optical surface relative to the laser eye surgery system. The OCT sample beam is focused within the patient's eye with the length of the reference path set to position the real portion detection window based on the location of the point on the optical surface such that the real portion detection window encompasses the optical surface for all expected variations in spatial disposition of the optical surface. Returning portions of the sample beam are processed so as to detect first locations on the optical surface within a first radial distance of the point on the optical surface. A first surface model of the optical surface is generated based on the location of the point on the optical surface and the first locations on the optical surface. Returning portions of the sample beam are processed so as to detect second locations on the optical surface beyond the first radial distance and within a second radial distance from the point on the optical surface. A second surface model of the optical surface is generated based on the location of the point on the optical surface and the first and second locations on the optical surface.

Variations of the method for processing optical coherence tomography (OCT) data to generate a surface model of an optical surface of a patient's eye are provided. For example, the optical surface can be the cornea anterior surface, the lens capsule anterior portion, or the lens capsule posterior portion. Processing returning portions of the sample beam so as to detect second locations can include generating a search volume defined by a first upper limit surface and a first lower limit surface. The first upper and lower limit surfaces can be offset from the first surface model on respective opposing sides of the first surface model. Processing returning portions of the sample beam focused at the plurality of different locations so as to detect second locations can be limited to the search volume. The method can include processing returning portions of the sample beam so as to detect third locations on the optical surface beyond the second radial distance and within a third radial distance from the point on the optical surface. The method can include generating a third surface model of the optical surface based on the location of the point on the optical surface and the first, second, and third locations on the optical surface. Processing returning portions of the sample beam so as to detect third locations can include generating a second search volume defined by a second upper limit surface and a second lower limit surface. The second upper and lower limit surfaces can be offset from the second surface model on respective opposing sides of the second surface model. Processing returning portions of the sample beam focused at the plurality of different locations so as to detect third locations can be limited to the second search volume. At least one of the first and second surface models can be an ellipsoid surface model or a spherical surface model. The optical surface can be the lens capsule anterior portion. A boundary surface within the detection window can divide the detection window into a real portion of the detection window and an imaginary portion of the detection window. The detection window imaginary portion can be disposed between the laser eye surgery system and the detection window real portion. Alternatively, the detection window real portion can be disposed between the laser eye surgery system and the detection window imaginary portion. When the optical surface is the lens capsule anterior surface, the reference path length can be set to position the lens capsule anterior surface between the detection window boundary surface and the laser eye surgery system. When the optical surface is the lens capsule posterior surface, the reference path length can be set to position the lens capsule posterior surface between the detection window boundary surface and the laser eye surgery system. The method can include calculating a transverse distance between an apex of the optical surface and a central axis of the laser eye surgery system. The method can include comparing the calculated transverse distance to a predetermined acceptable transverse distance value. The method can include inhibiting treatment of the patient's eye if the calculated transverse distance exceeds the predetermined acceptable transverse distance value.

In another aspect, a method is provided for identifying optical surfaces in an eye for performing laser surgery on the eye. The eye includes a cornea having anterior and posterior surfaces, a lens capsule having anterior and posterior surfaces, an iris, a pupil, and a limbus. The method includes coupling the eye to a laser eye surgery system that includes an optical coherence tomography (OCT) imaging subsystem, the OCT imaging subsystem including a reference path length that is adjustable so that a distance from the laser eye surgery system to a detection window of the OCT imaging subsystem is adjustable, the OCT imaging subsystem employing a detection beam having a plurality of wavelengths such that the detection window spans a range of distances relative to the laser eye surgery system; using the OCT imaging subsystem to locate a centrally-located point on the lens capsule anterior surface; directing an OCT sample beam into the eye with the reference path length set to position the detection window to encompass the lens capsule anterior surface and the iris; processing returning portions of the sample beam to identify, relative to the laser eye surgery system, a plurality of edge points within the detection window, each edge point being disposed on an optical surface; generating a surface model of the lens capsule anterior surface based on the location of the centrally-located point on the lens capsule anterior surface and a subset of the edge points; selecting a subset of the edge points that are offset from the surface model of the lens capsule anterior surface; and generating a surface model of the iris based on the subset of the edge points that are offset from the surface model of the lens capsule anterior surface.

Variations of the method for identifying optical surfaces in an eye for performing laser surgery on the eye are provided. For example, the surface model of the iris can be an oriented plane. The method can include using the OCT imaging subsystem to generate a surface model of the cornea anterior surface; generating a curved-line intersection between the iris surface model and the cornea anterior surface model; and using the curved-line intersection to represent the location of the limbus. The method can include processing a video image of the eye to identify the pupil by searching outwardly from a central location to identify edges of the iris. The method can include generating a curved-line model of the pupil based on the video identified pupil and the iris surface model.

In another aspect, a method is provided for generating a surface model of a posterior surface of a cornea of an eye, the cornea having an anterior surface. The method includes coupling the eye to a laser eye surgery system that includes an optical coherence tomography (OCT) imaging subsystem, the OCT imaging subsystem including a reference path length that is adjustable so that a distance from the laser eye surgery system to a detection window of the OCT imaging subsystem is adjustable, the OCT imaging subsystem employing a detection beam having a plurality of wavelengths such that the detection window spans a range of distances relative to the laser eye surgery system; directing an OCT sample beam into the eye with the reference path length set to position the detection window to encompass the cornea; generating a search volume defined by a first upper limit surface and a first lower limit surface, the first upper and lower limit surfaces being offset from a surface model of the cornea anterior surface; and processing returning portions of the OCT sample beam corresponding to the search volume to identify points located on the cornea posterior surface. In many embodiments, at least one of the first upper and lower limit surfaces is a sphere, an ellipsoid, or a conicoid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9C illustrates an OCT scan pattern having multiple focus depths, in accordance with many embodiments.

FIG. 10E shows a detected edge relative to the original OCT scan data of FIG. 10C, in accordance with many embodiments.

DETAILED DESCRIPTION

System Configuration

Figure 1:
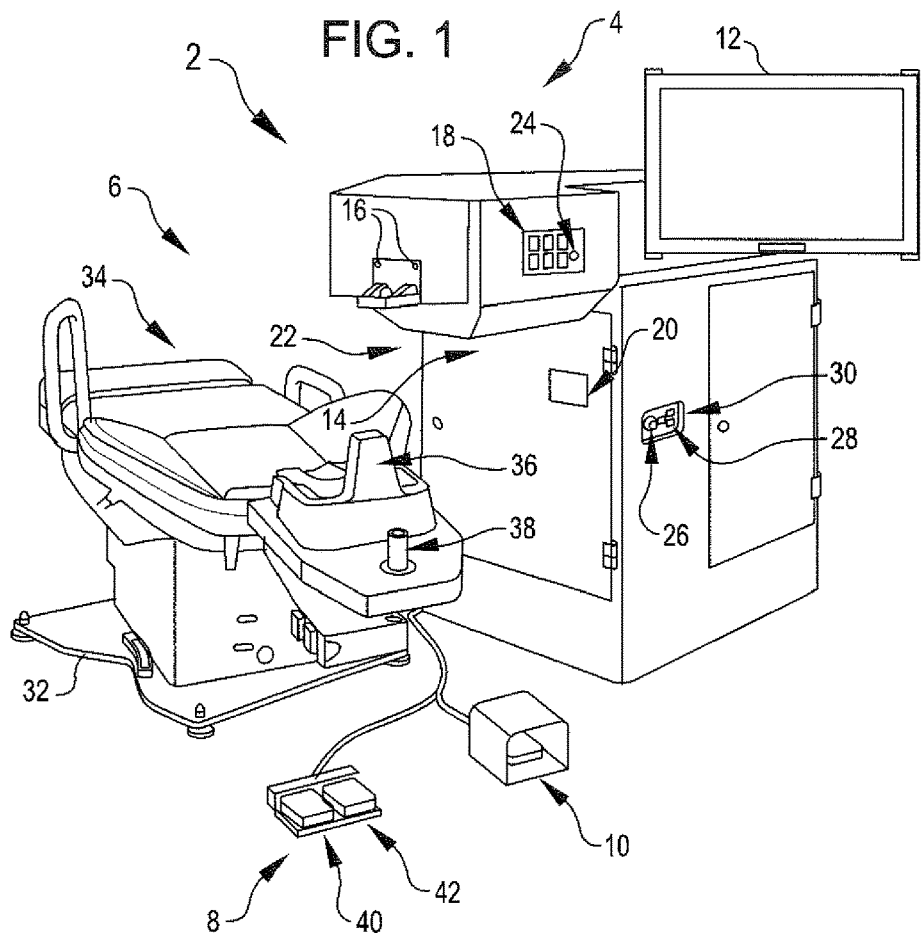
FIG. 1 is a perspective view showing a laser eye surgery system, in accordance with many embodiments.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
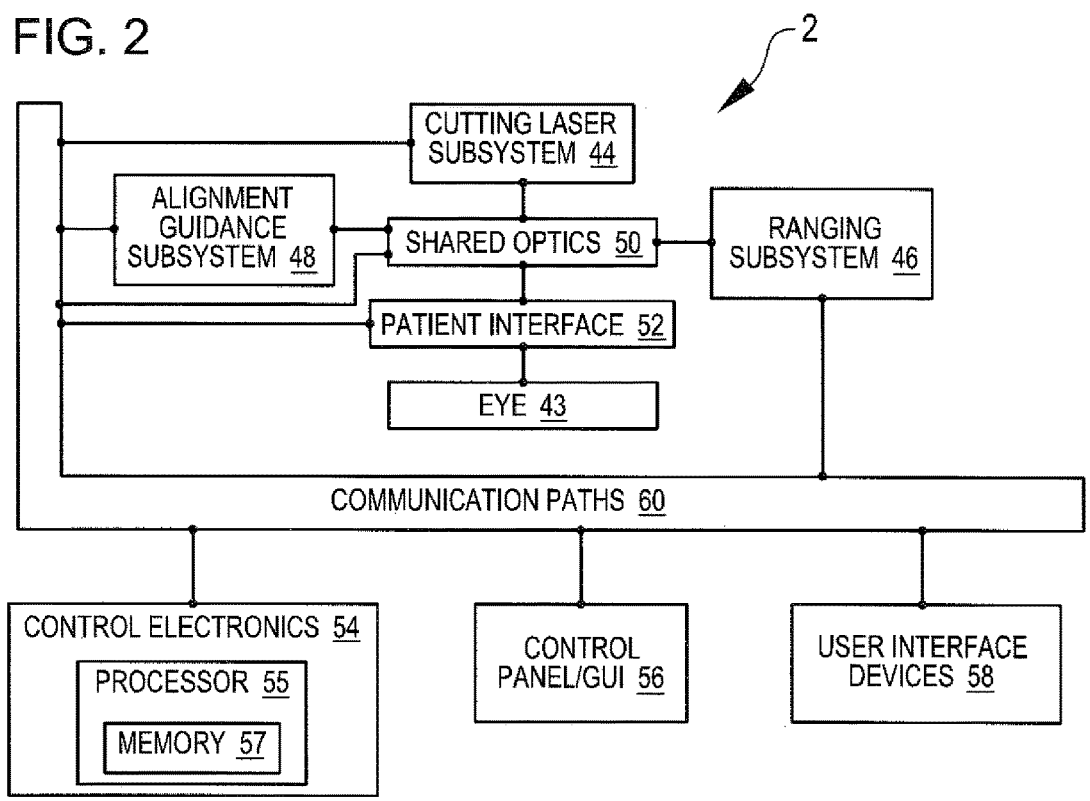
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
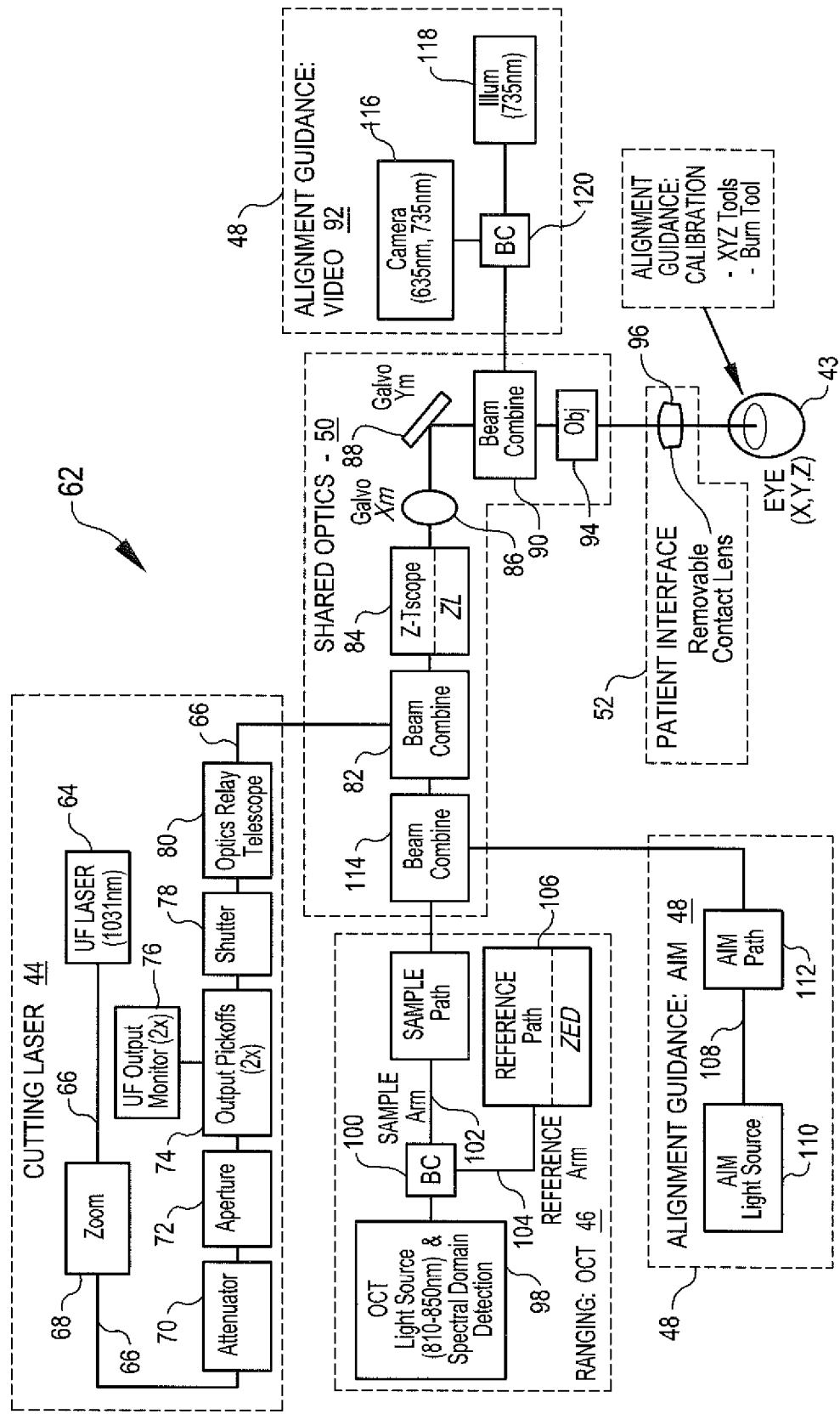
FIG. 3 is a simplified diagram illustrating the configuration of an optical assembly of a laser eye surgery system, in accordance with many embodiments.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically, to achieve optimal performance the transmission through this aperture is set at between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a Z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-scan device 86 and the Y-scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source may be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 4:
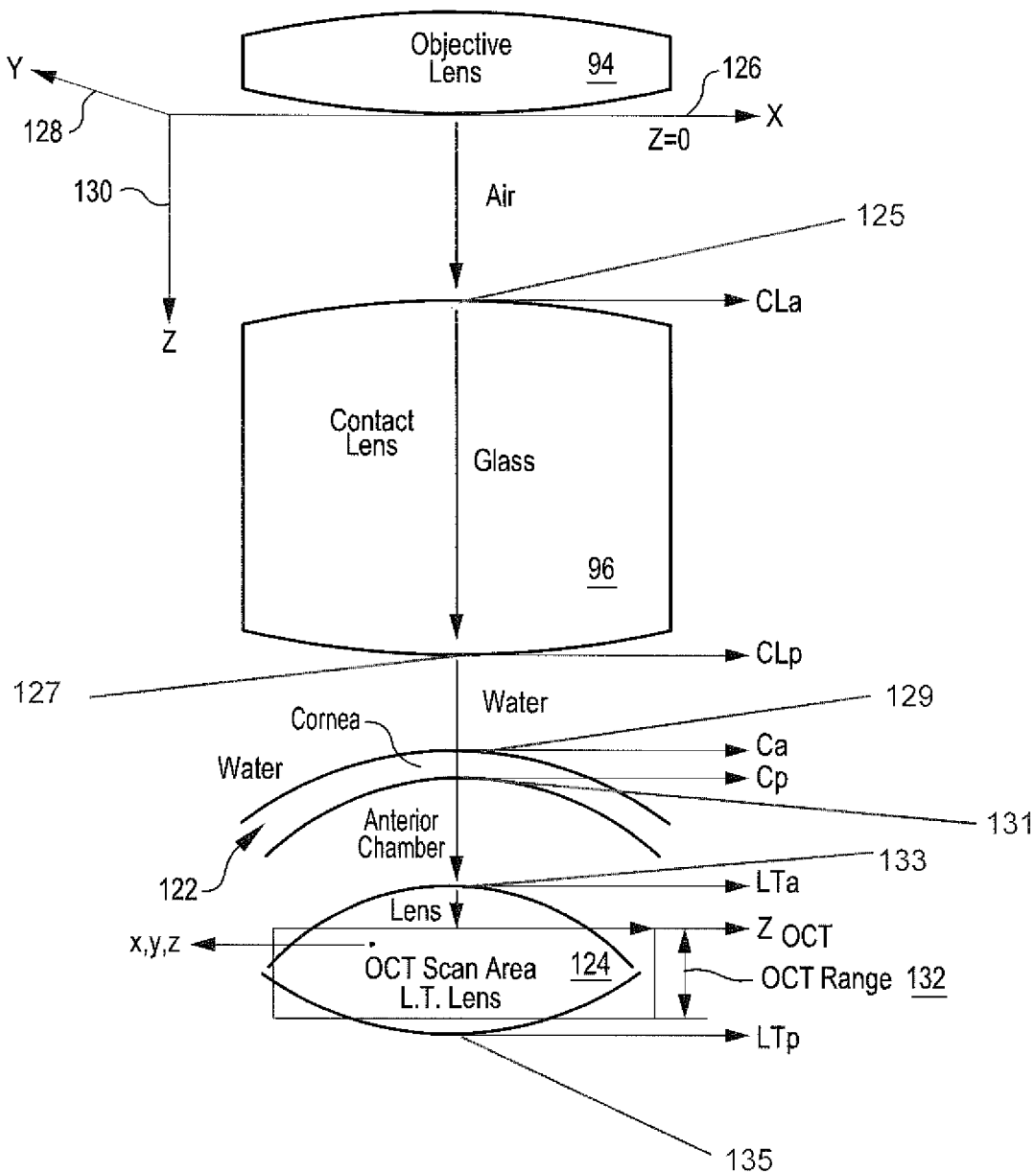
FIG. 4 is a simplified schematic diagram illustrating structures that can be measured by a laser eye surgery system, in accordance with many embodiments.

FIG. 4 is a simplified schematic diagram illustrating structures that can be measured by the laser eye surgery system 2. Structures that can be measured by the laser eye surgery system 2 (relative to the laser eye surgery system 2) include, but are not limited to, the patient interface lens 96, the cornea 122 of the patient's eye 43, and the lens 124 of the patient's eye 43. Measurements that can be accomplished by the laser eye surgery system 2 include the distance (CLa) to the anterior surface 125 (e.g., apex or in close proximity to the apex) of the patient interface lens 96 from the objective lens 94, the distance (CLp) to the posterior surface 127 (e.g., apex or in close proximity to the apex) of the patient interface lens 96 from the objective lens 94, the distance (Ca) to the anterior surface 129 (e.g., apex or in close proximity to the apex) of the cornea 122 from the posterior surface 127 of the patient interface lens 96, the location of points on the anterior surface 129 of the cornea 122, the distance (Cp) to the posterior surface 131 (e.g., apex or in close proximity to the apex) of the cornea 122 from the posterior surface 127 of the patient interface lens 96, the location of points on the posterior surface 131 of the cornea 122, the distance (LTa) to the anterior surface 133 (e.g., apex or in close proximity to the apex) of the lens 124 from the posterior surface 127 of the patient interface lens 96, the location of points on the anterior surface 133 of the lens 124, the distance (LTp) to the posterior surface 135 (e.g., apex or in close proximity to the apex) of the lens 124 from the posterior surface 127 of the patient interface lens 96, and the location of points on the posterior surface 135 of the lens 124. Although not shown in FIG. 4, the iris, pupil, and limbus of the patient's eye 43 can also be measured/located by the laser eye surgery system 2.

The laser eye surgery system 2 is configured to use the ranging subsystem 46 and the shared optics 50 to measure/locate the patient interface lens 96, the cornea 122, the lens 124, the iris, the pupil, and the limbus. The laser eye surgery system 2 can also employ the alignment guidance system 48 to measure/locate the iris, the pupil, and the limbus. The shared optics 50 is used to control the direction of the OCT sample portion beam 102 emitted from the shared optics 50 toward the patient interface lens 96. At least a portion of the OCT sample portion beam 102 continues through the patient interface lens 96 and into the patient's eye. The OCT sample portion beam 102 is scanned in X direction 126 by the X-scan device 86 and in the Y-direction 128 by the Y-scan device 88. The OCT sample portion beam 102 is also focused onto different focus points in the Z-direction 130 by the Z-telescope 84. Although shown offset in FIG. 4, the Z axis is aligned with the optical centerlines of the objective lens 94 and the patient interface lens 96. By selectively setting the length of the reference path 106, the location of a detection window 132 in the Z-direction 130 can be selected. A small portion of the OCT sample portion beam 102 reflects from a structure within the detection window 132 and travels back through the shared optics 50 and into the OCT light source and detection device 98, where the returning reflected light is analyzed in combination with the returning OCT reference portion beam 104 to determine the Z-direction distance of the structure from which the small portion of the OCT sample portion beam 102 was reflected. The determined Z-direction distance, in combination with the associated X direction and Y direction of the emitted OCT sample portion beam 102 as directed by the X-scan device 86 and the Y-scan device 88, is used to determine the X, Y, and Z coordinates of the structure from which the OCT sample portion beam 102 was reflected, thereby locating the structure relative to the laser eye surgery system 2.

In many embodiments, the patient interface lens 96 is part of a disposable assembly that is used for one treatment and then replaced with a new patient interface lens 96. Variability in the disposable lens assembly, however, may be significant enough to impact the positional accuracy of the scanning of the treatment beam 66 and/or the OCT sample portion beam 102 downstream of the patient interface lens. Accordingly, in many embodiments, the location of the anterior and posterior surfaces of the patient interface lens 96 are measured via the ranging subsystem 46 and used to compensate for the characteristics of the specific patient interface lens 96 used in a treatment.

OCT Scanning Methods

Figure 5:
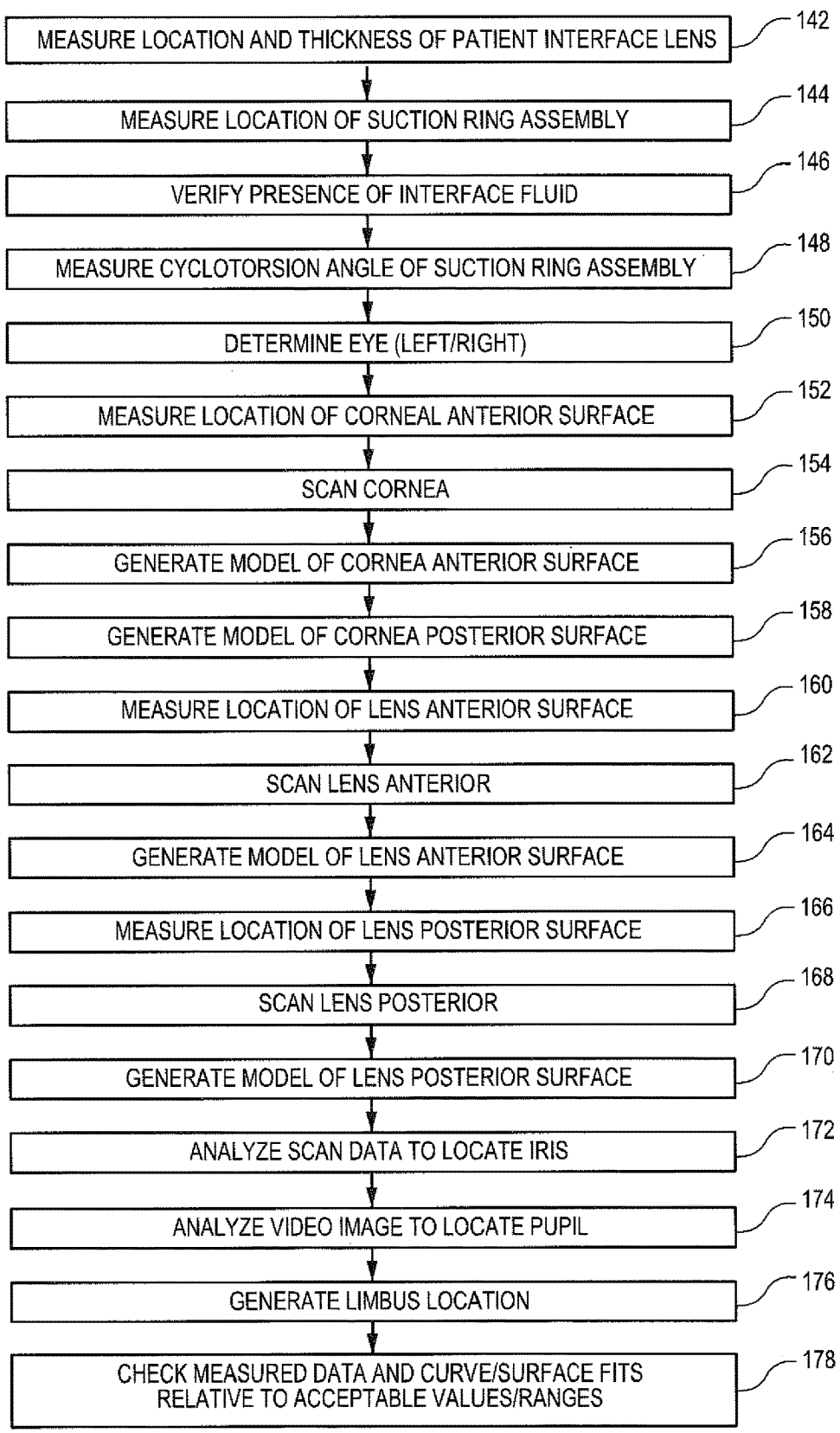
FIG. 5 is a simplified block diagram of acts of a method for automatically generating surface models and curved line models that accurately represent the spatial disposition of optical surfaces and structures of the patient's eye relative to a laser eye surgery system, in accordance with many embodiments.

FIG. 5 are simplified diagrams illustrating a method 140 for automatically generating surface models and curved line models that accurately represent the spatial disposition of optical surfaces and structures of the patient's eye 43 relative to the laser eye surgery system 2. The method 140 can be practiced using any suitable systems, devices, and acts, such as using any suitable systems, devices, and acts described herein. While the acts of the method 140 are listed in a particular order, any suitable execution order of the acts can be used.

In act 142, the location and thickness of the patient interface lens 96 are measured. For example, the ranging subsystem 46 can be used to measure the distance (CLa) to the anterior surface 125 (e.g., apex or in close proximity to the apex) of the patient interface lens 96 and the distance (CLp) to the posterior surface 127 (e.g., apex or in close proximity to the apex) of the patient interface lens 96. The measured CLa and CLp can be checked by comparison with suitable maximum and minimum acceptable values.

In many embodiments, the patient interface 52 includes a patient interface lens assembly and a suction ring assembly. The patient interface lens assembly includes the patient interface lens 96 and is demountably coupled to the laser eye surgery system 2. In many embodiments, the suction ring assembly is demountably vacuum coupled to the patient's eye 43 and is then demountably vacuum coupled to the patient interface lens assembly. In act 144, the ranging subsystem 46 is used to measure the location of the suction ring assembly. For example, the suction ring assembly can include a reference surface that is located by the ranging subsystem 46. The measured location of the suction ring assembly can be checked by comparison with suitable maximum and minimum values.

In act 146, the ranging subsystem 46 is used to verify the presence of interface fluid between the posterior surface of the patient interface lens 96 and the patient's eye 43. For example, the ranging subsystem 46 can be used to measure the distance to a reference surface of the suction ring assembly, which is disposed between the posterior surface 127 of the patient interface lens 96 and the patient's eye 43. Due to the different indexes of refraction of air and the interface fluid, the measured distance to the reference surface of the suction ring assembly will differ depending on whether the interface fluid is present or missing.

In act 148, the ranging subsystem 46 is used to measure the cyclotorsion angle of the patient interface 52 relative to the laser eye surgery system 2. The suction ring assembly can include a handle that requires that the suction ring assembly be coupled with the patient's eye such that the handle can only extend to the side of the patient to avoid interference between the handle and the patient. The suction ring assembly can also include fiducial features located to be measured by the ranging subsystem 46 to determine the position and the cyclotorsion angle of the suction ring assembly relative to the laser eye surgery system 2. The cyclotorsion angle of the suction ring assembly can be checked by comparison with suitable maximum and minimum values. The cyclotorsion angle of the suction ring, in combination with the fact that the handle can only extend to the side of the patient, can be used to determine which eye the suction ring assembly is coupled to (act 150).

In many embodiments, the ranging subsystem 46 is used to measure the spatial disposition of the cornea 122 and the lens 124. For example, in act 152, the ranging subsystem 46 is used to measure the location of the cornea anterior surface 129. In act 154, the ranging subsystem 46 is used to obtain cornea scan data that can be processed to locate the cornea anterior surface 129 and the cornea posterior surface 131. In act 156, the cornea scan data is processed to generate a surface model of the cornea anterior surface. In act 158, the cornea scan data is processed to generate a surface model of the cornea posterior surface 131. In act 160, the ranging subsystem 46 is used to measure the location of the lens anterior surface 133. In act 162, the ranging subsystem 46 is used to obtain lens anterior surface scan data that can be processed to locate the lens anterior surface 133. In act 164, the lens anterior scan data is processed to generate a surface model of the lens anterior surface. In act 166, the ranging subsystem 46 is used to measure the location of the lens posterior surface 135. In act 168, the ranging subsystem 46 is used to obtain lens posterior surface scan data that can be processed to locate the lens posterior surface 135. In act 170, the lens posterior scan data is processed to generate a surface model of the lens posterior surface. In act 172, scan data obtained using the ranging subsystem 46, for example, the lens anterior surface scan data, is processed to generate a surface model of the iris of the patient's eye 43. In act 174, a video image of the patient's eye 43 is processed to identify the pupil of the patient's eye 43. In act 176, a curved line representing the location of the limbus of the patient's eye 43 is generated. For example, the curved line representing the limbus can be generated by intersecting an oriented plane surface model of the iris and the surface model of the cornea anterior surface. In act 178, the location data, the curved-line models, and the surface models of structures of the patient's eye 43 can be checked via comparison with suitable values and/or ranges of values.

FIG. 5 illustrates method 140 in accordance with embodiments. Many variations of the method 140 can be performed in accordance with embodiments. The acts of method 140 may comprise steps. The steps can be performed in any order, the steps can be removed, added or repeated. The steps may comprise sub-steps.

The circuitry of system 2 as described herein, for example the processor of system 2, can be configured with instructions to perform one or more of the steps of the method 140, and the tangible medium of the processor may embody instructions to perform one or more of the steps of method 140. In many embodiments, the tangible medium comprises instructions of a computer readable memory having instructions of a computer program to perform one or more of the steps of the method 140. Alternatively or in combination, the logic array, such as the field programmable gate array as described herein can be programmed to perform one or more of the steps of method 140. In many embodiments, the processor comprises a plurality of processors and may comprise a plurality of distributed processors.

Measuring the Patient Interface Lens

Figure 6:
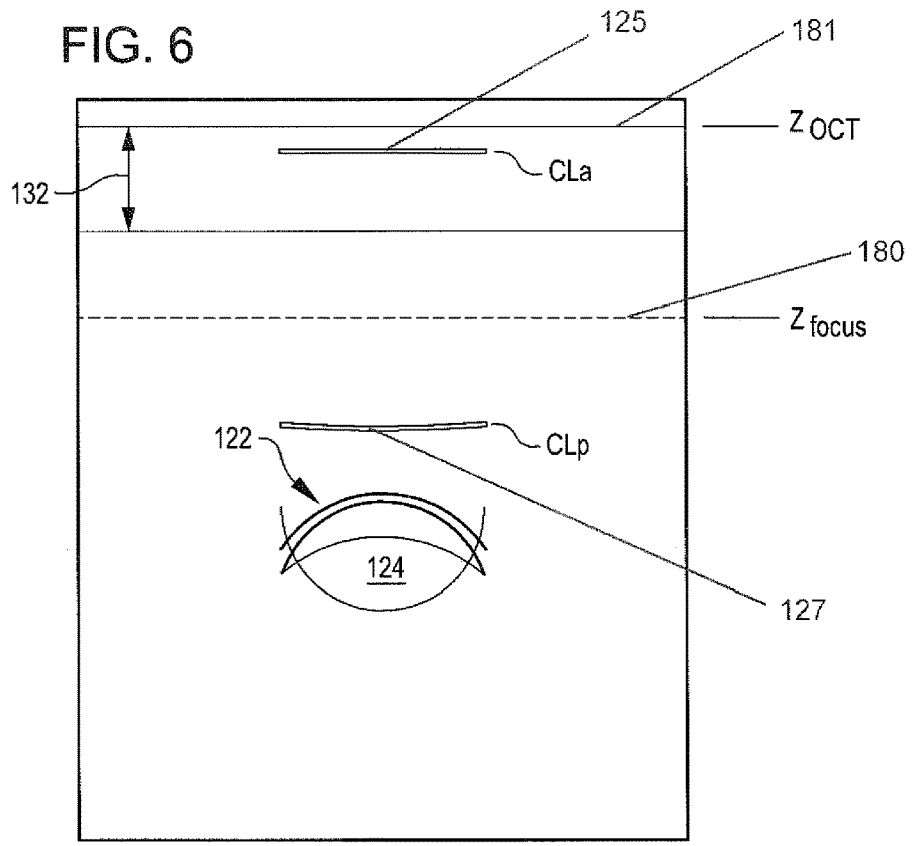
FIG. 6 is a simplified diagram illustrating aspects of an OCT scan used to measure the location of an anterior surface of a patient interface lens of a laser eye surgery system, in accordance with many embodiments.
Figure 7:
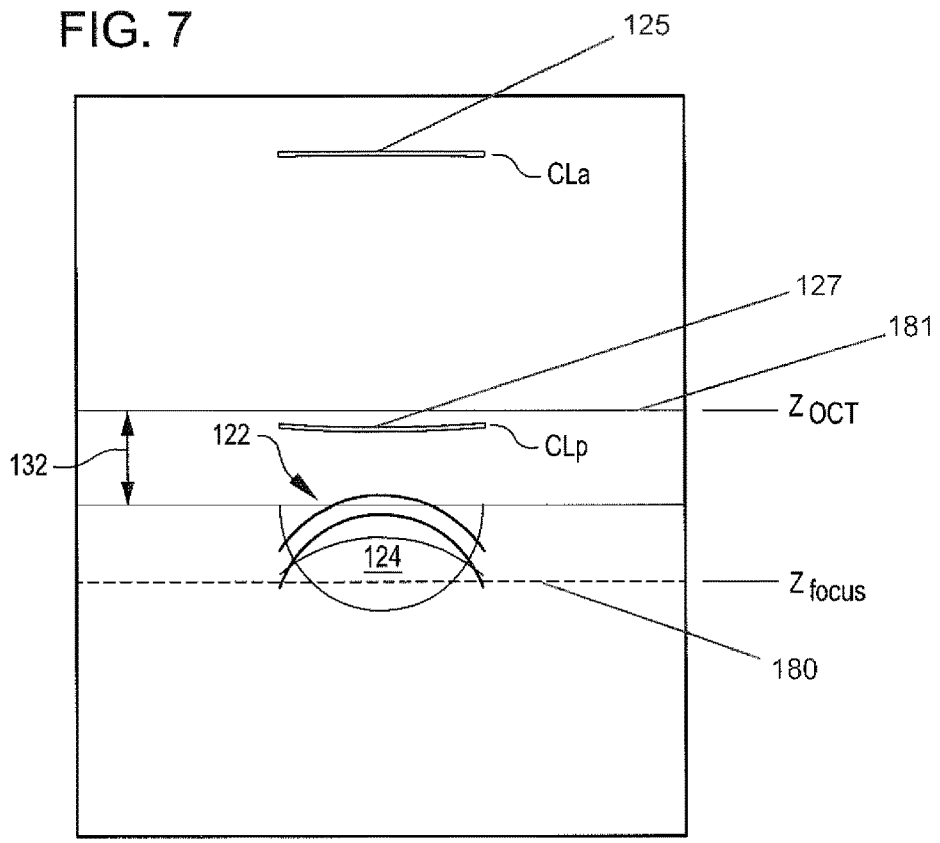
FIG. 7 is a simplified diagram illustrating aspects of an OCT scan used to measure the location of a posterior surface of a patient interface lens of a laser eye surgery system, in accordance with many embodiments.

FIG. 6 is a simplified diagram illustrating the measurement of the distance (CLa) to the anterior apex of the patient interface lens 96 from the objective lens 94. FIG. 7 is a simplified diagram illustrating the measurement of the distance (CLp) to the posterior apex of the patient interface lens 96 from the objective lens 94. Items represented in FIG. 6 and FIG. 7 include the detection window 132, which has an upper limit at $Z_{OCT}$, the anterior surface 125 of the patient interface lens 96, the posterior surface 127 of the patient interface lens 96, a focus depth 180 ($Z_{focus}$) at which the OCT sample portion beam 102 is focused by the Z-telescope 84, the cornea 122, and the lens 124. Because the surfaces of the patient interface lens 96 generate strong reflections, the respective focus depth 180 ($Z_{focus}$) for the OCT sample portion beam 102 is located below the respective surface being measured so as to reduce the amount of light reflected from the respective surface back to the OCT light source and detection device 98.

In many embodiments, the detection window 132 is a real portion of a larger detection window that includes a detection window imaginary portion. In many embodiments, the upper limit 181 at $Z_{OCT}$ is a boundary surface that separates the detection window real and imaginary portions. In the described embodiments, the detection window imaginary portion is disposed between the detection window real portion and the laser eye surgery system 2. In alternate embodiments, the detection window real portion can be disposed between the detection window imaginary portion and the laser eye surgery system 2. The use of the terms real portion and imaginary portion refers to the analysis of the returning sample and reference beams by the OCT light source and detection device 98.

The scanning strategy used to determine the location of the anterior and posterior surfaces of the patient interface lens 96 will now be described. The variables CLa (actual-measured), CLan (nominal location for a population of patient interface lenses 96), CLp (actual-measured), and CLpn (nominal for a population of patient interface lenses 96) represent the physical locations of the anterior and posterior surfaces 125, 127 of the patient interface lens 96 referenced to the posterior surface of the objective lens 94. $Z_{oct}$ is the location of the first pixel of the OCT A-scan.

CLp can be used for various suitable purposes. For example, CLp can be used to transform Cartesian coordinates of the OCT point (X, Y, $Z_{focus}$) to the galvo directives (Xm, Ym and Zl) via a look-up table for the Z-telescope 84 ($LUT_{Z1}$). While CLp may not be running variable in a look-up table for the adjustable reference path 106 ($LUT_{ZED}$), CLp can be used as a parameter to determine the usability range of the look-up table for the adjustable reference path 106 ($LUT_{ZED}$). CLa and CLp can be used to transform the absolute $Z_{oct}$ (referenced from the objective) to the $Z_{oct}$|CLp (referenced from the patient interface lens 96).

In order to speed up scheduling and execution of the steps to determine CLa and CLp, some of the tasks required can be performed concurrently. The OCT scans used to determine CLa and CLp cannot occur concurrently because there is only one OCT system. The OCT scan used to determine CLp, however, can be accomplished before the computation of CLa (based on CLan) is accomplished. Accordingly, a temporary CLp* can be obtained that is based on CLan. A subsequent step corrects the temporary CLp* into the real CLp based on the newly computed (and real) CLa.

An example procedure for measuring CLa and CLp begins with using the corresponding default nominal values (e.g., CLan=21.72 mm, CLpn=33.72 mm). A group of A-scans arranged as a small spiral is commanded to determine the CLa location with:

$$Zed_{commanded} = \frac{CLan - \Delta}{2}$$

$$Z_{focus}|_{CLpn} = CLan + \gamma - CLpn$$

$$Z_l = LUT_{Z1}(x, y, Z_{focus}|_{CLpn}, CLp = CLpn)$$

$\Delta$ is selected and used to offset the top of the OCT detection window 132 above CLan such that the OCT detection window is positioned to encompass all expected variations in the actual position of the anterior surface 125 of the patient interface lens 96. The factor of two reflects the configuration of the adjustable OCT reference path 106 in which a change in $Zed_{commanded}$ results in double the change in length of the OCT reference path 106. The distance y focuses the OCT scan away from the surface so as to avoid its glare. $Z_{focus}|_{CLpn}$ is referenced to CLpn. This introduces an approximation in the focusing location that has not significant implications since the signal from the patient interface lens is very strong.

Due to Zed location variability, the CLa OCT scan is performed at a different Zed ($Zed_{commanded} \neq Zed_{actual}$) so that the OCT scan depth is:

$$Z_{OCT\text{-}actual}(X,Y) = Zed_{actual}*2 + n_{water}*LUT_{Zed}(X,Y)$$

The CLa location is computed by taking the median of the transformed pixel position of the surface points as:

$$CLa = Zed_{actual}*2 + \text{Median}\left[n_{water}*LUT_{Zed}(X_n, Y_n) + n_{water}\frac{R_{water}}{511}Pixel_n\right]$$

$R_{water}$ is the range of the OCT scan in water. $Pixel_n$ is indicative of the depth of the reflecting structure within the OCT detection window 132. The LUT value and the mm to pixel transformation are scaled by the water index of refraction because the LUT and the OCT range assume distances in water.

After performing the OCT scan to measure CLa, a group of A-scans arranged as a small spiral is commanded to determine the temporary CLp* location. Note that the actual anterior patient interface lens surface (CLa) may not yet have been calculated (e.g., for scheduling purposes it may be beneficial to proceed with performing the OCT scan to measure CLp before CLa has been calculated) and the approximation CLan is used instead. Subsequently, a correction is performed to calculate CLp from CLp*. Referring to FIG. 7, the OCT scan to measure CLp* is commanded with:

$$Zed_{commanded} = \frac{(CLan + (CLpn - CLan)*n_{glass} - \Delta)}{2}$$

$$Z_{focus}|_{CLpn} = \gamma$$

$$Z_l = LUT_{OCTZ1}(x, y, Z_{focus}|_{CLpn} =, CLp = CLpn)$$

Due to Zed variability, the OCT scan to measure CLp* is performed at $Zed_{actual}$. Using an assumption that the anterior surface 125 of the patient interface lens 96 is located at CLan, CLp* can be determined using:

$$Z_{OCT}(0,0) = \frac{2*Zed_{actual} - CLan}{N_{glass}} + CLan$$

$$CLp^* =$$

$$Z_{OCT}(0,0) + \text{Median}\left[\frac{n_{water}}{n_{glass}}*LUT_{Zed}(X_n, Y_n) + \frac{n_{water}}{n_{glass}}\frac{R_{water}}{511}Pixel_n\right]$$

$$CLp^* = \frac{2*Zed_{actual}}{N_{glass}} + CLan\left(\frac{N_{glass}-1}{N_{glass}}\right) +$$

$$\text{Median}\left[\frac{n_{water}}{n_{glass}}*LUT_{Zed}(X_n, Y_n) + \frac{n_{water}}{n_{glass}}\frac{R_{water}}{511}Pixel_n\right]$$

Because CLp* is based on the assumption that the anterior surface 125 of the patient interface lens 96 is located at CLan, a subsequent correction based on the actual position (CLa) of the anterior surface of the patient interface lens 96 is performed. Once CLa has been determined, CLp can be calculated using:

$$CLp = \frac{2*Zed_{actual}}{N_{glass}} + CLa\left(\frac{N_{glass}-1}{N_{glass}}\right) +$$

$$\text{Median}\left[\frac{n_{water}}{N_{glass}}*LUT_{Zed}(X_n, Y_n) + \frac{n_{water}}{n_{glass}}\frac{R_{water}}{511}Pixel_n\right]$$

So that $$Clp = CLp^* + \left(\frac{N_{glass}-1}{N_{glass}}\right)(Cla - Clan)$$

Once CLa and CLp have been determined, a new set of variables (Z and Zed) can be defined relative to CLp.

$$Zed @ CLp = \frac{CLa + (CLp - CLa)n_{glass}}{2}$$

$$Zed\,|_{CLp} = Zed - Zed @ CLp$$

$$Z\,|_{CLp} = Z - CLp$$

Measuring the Suction Ring Assembly

Figure 8A:
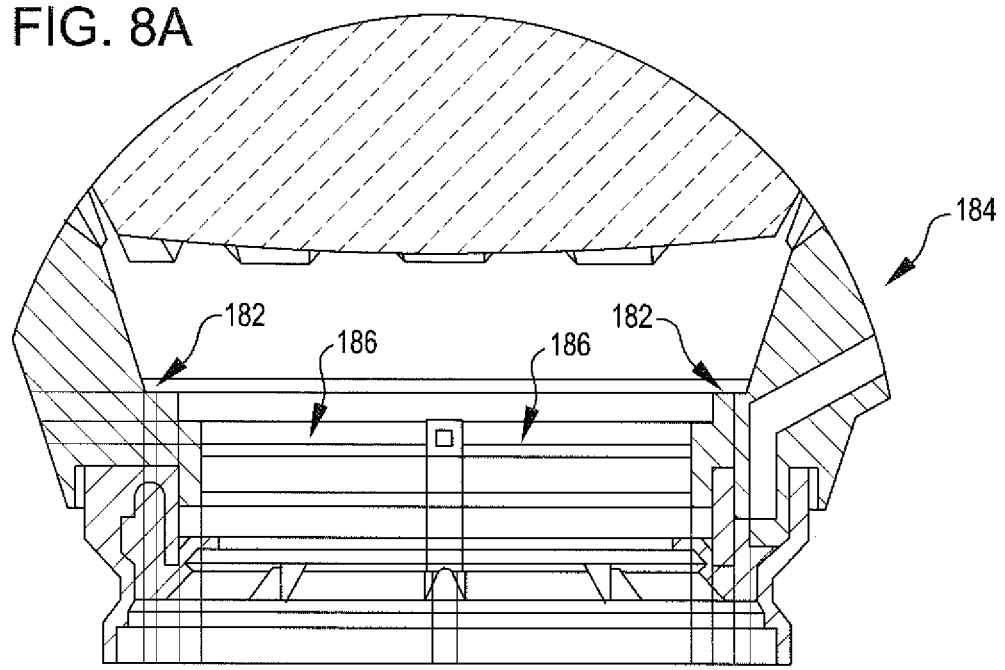
FIG. 8A is a cross-sectional view of a suction ring assembly having a reference surface that is locatable by an OCT scan, in accordance with many embodiments.
Figure 8B:
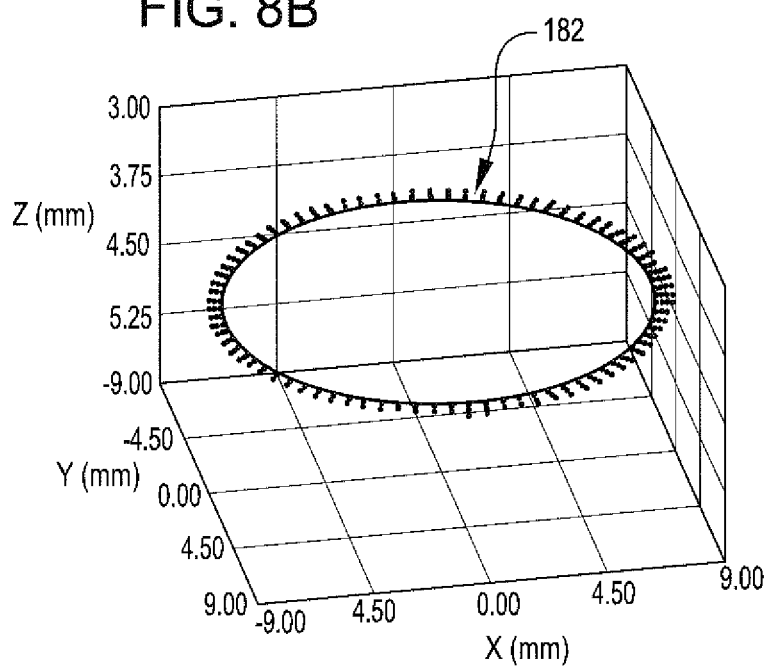
FIG. 8B illustrates OCT measured locations of the reference surface of FIG. 8A when the suction ring has been correctly docked to a laser eye surgery system, in accordance with many embodiments.
Figure 8C:
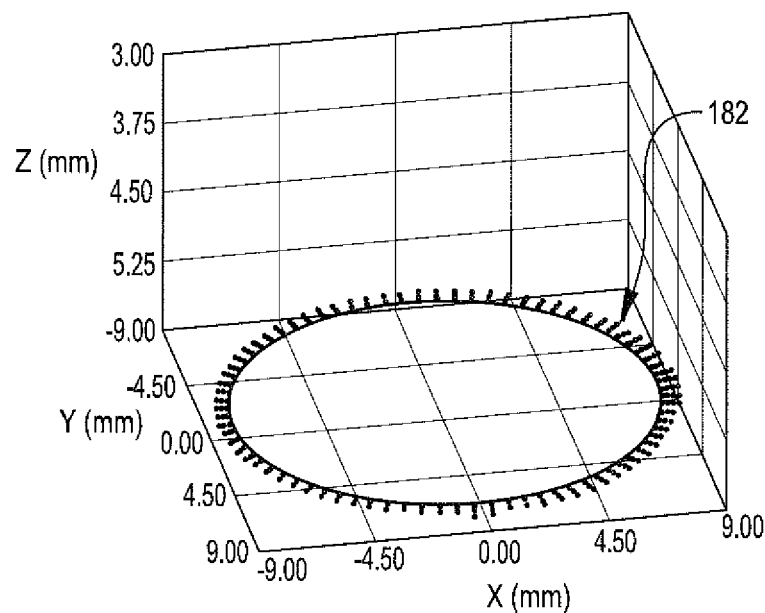
FIG. 8C illustrates OCT measured locations of the reference surface of FIG. 8A when the suction ring has been incorrectly docked to a laser eye surgery system, in accordance with many embodiments.
Figure 8D:
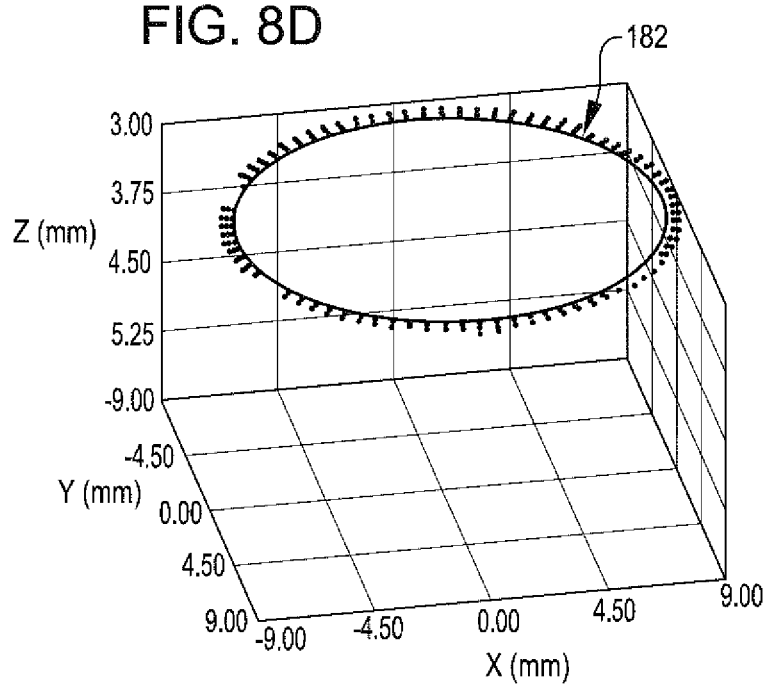
FIG. 8D illustrates OCT measured locations of the reference surface of FIG. 8A when interface fluid is missing between a patient interface lens and a patient's eye, in accordance with many embodiments.

A set of A-scans arranged as spiral whose points are aligned in radiuses can be performed to detect a surface 182 of a suction ring assembly 184 depicted in FIG. 8A. By using the ranging subsystem 46 to locate the surface 182, the x, y center of the suction ring assembly 184 can be determined. It can also be used to determine whether the interface liquid (e.g., a sterile buffered saline solution (BSS) such as Alcon BSS (Alcon Part Number 351-55005-1) or equivalent) is present between the patient interface lens 96 and the patient's eye 43. It can also be used to detect if the suction ring assembly 184 is correctly docked in place relative to the laser eye surgery system 2. For example, FIG. 8B shows an example location of the surface 182 when the suction ring assembly 184 is correctly docked (e.g., surface 182 is at 4.2 mm). In contrast, FIG. 8C shows an example location of the surface 182 when the suction ring assembly 184 is incorrectly docked (e.g., surface 182 is at 5.6 mm). FIG. 8D shows an example measured location of the surface 182 when the interface liquid is missing from the suction ring assembly 184 (e.g., the surface 182 appears to at 3.2 mm due to difference in refractive index between air and the interface liquid). The x, y center is used in the determination of the cyclotorsional orientation of the patient interface.

Cyclotorsion Angle Measurement and Eye (R/L) Type

A set of A-scans arranged as a ring is performed to detect a surface 186 of the suction ring assembly 184 depicted in FIG. 8A. The surface 186 contains 3 notches at the 0, Pi/2 and Pi locations. The results of the OCT scan are convoluted with a template that is shifted until a best match is achieved. The resulting orientation of the template is indicative of the cyclotorsion angle of the suction ring assembly 184 relative to the laser eye surgery system 2. In many embodiments, the suction ring assembly 184 has a protruding handle that extends sideways from the suction ring assembly 184. As a result, the suction ring assembly 184 can only be coupled with the patient's eye such that the protruding handle extends to the side of the patient to avoid interference between the protruding handle and the patient. Accordingly, the resulting orientation of the template is indicative of which eye the suction ring assembly 184 is coupled with.

Figure 8E:
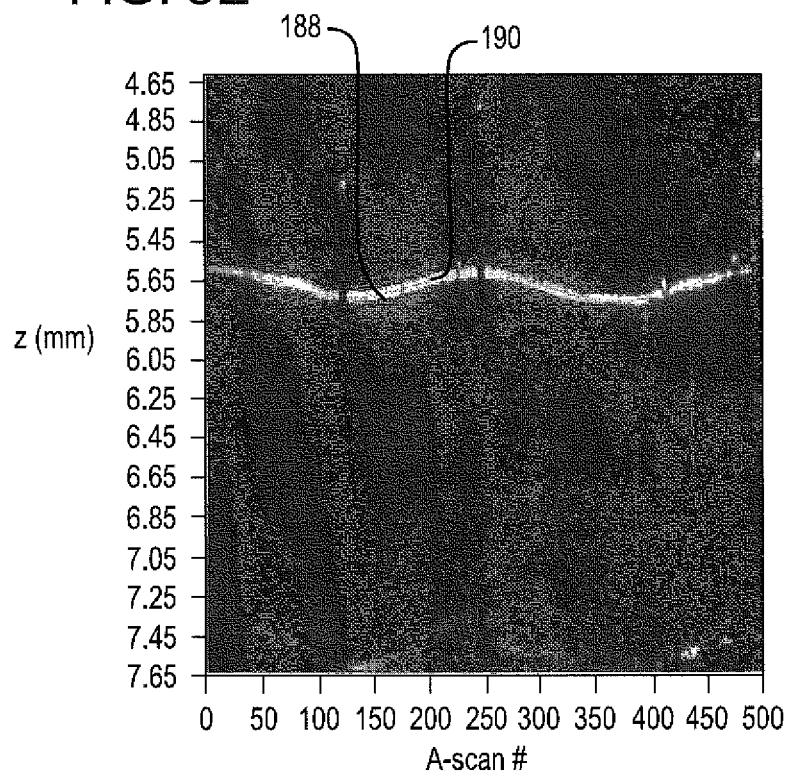
FIG. 8E illustrates a template matched to an OCT generated image of a reference surface of the suction ring of FIG. 8A, in accordance with many embodiments.

FIG. 8E shows a return signal 188 from the ranging subsystem 46. The return signal 188 exhibits three displaced segments, corresponding to the three notches at the 0, Pi/2 and Pi locations in the surface 186. A line 190 represents a best match fit of the template to the surface 186 and the three notches at the 0, Pi/2 and Pi locations in the surface 186.

Anterior Cornea Prescan

Figure 9A:
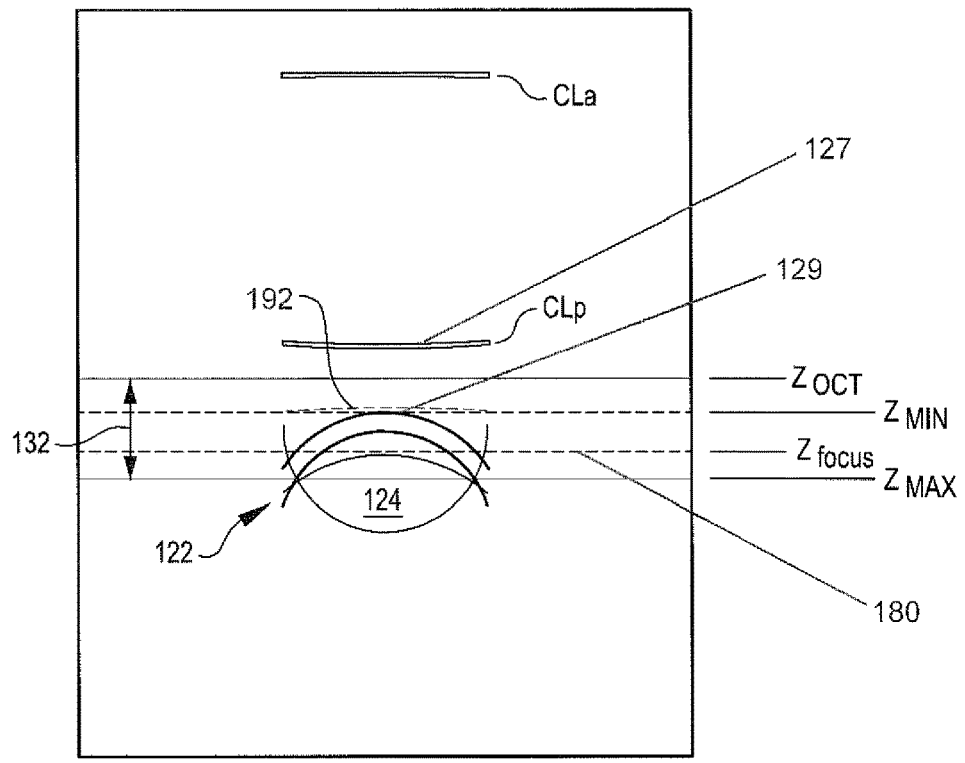
FIGS. 9A and 9B are simplified diagrams illustrating aspects of an OCT scan used to measure the location of an anterior surface of a cornea, in accordance with many embodiments.
Figure 9B:
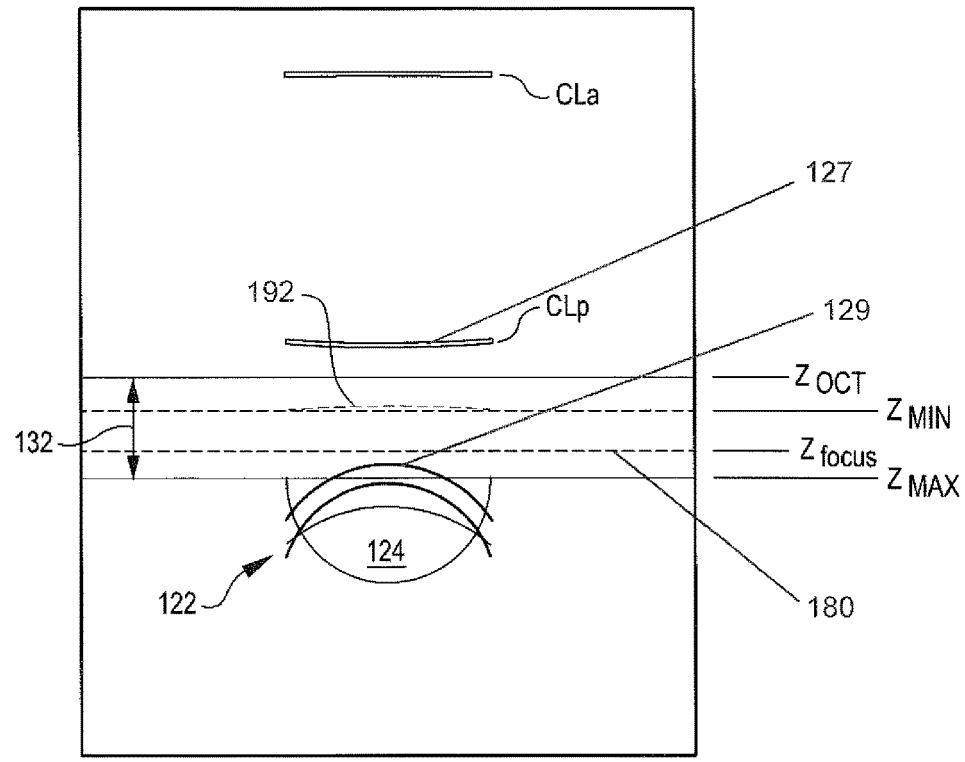

A group of A-scans arranged as a spiral is commanded to determine the z position of the anterior surface 129 of the cornea 122 (e.g., the apex of the cornea anterior surface 129 on in close proximity to the apex). A plane can be defined that includes the z position of the anterior surface 129 of the cornea 122. The plane can be used during subsequent determination of a surface model for the anterior surface 129 of the cornea 122. As illustrated in FIGS. 9A and 9B, the anterior cornea prescan can be commanded with:

$$Zoct_{commanded}\,|_{CLp} = \frac{WaterGap_{min}}{2} - \delta$$

$$Zed_{commanded}\,|_{CLp} = \left(\frac{WaterGap_{min}}{2} - \delta\right)\frac{n_{water}}{2}$$

$$Zfocus\,|_{CLp} = WaterGap_{nom}$$

$$Z_l = LUT_{OCT\,Zl}(X, Y, Zfocus\,|_{CLp}, CLp)$$

Due to variations CLp and natural variations in the z position of the anterior surface 129 of the cornea 122, there are a range of possible positions of the anterior surface 129 of the cornea 122. For example, FIG. 9A illustrates a minimum gap between the anterior surface 129 of the cornea 122 and the posterior surface 127 of the patent interface lens 96. In contrast, FIG. 9B illustrates a minimum gap between the anterior surface 129 of the cornea 122 and the posterior surface 127 of the patent interface lens 96. The OCT detection window 132 is selected such that the anterior cornea surface is detectable in both extremes and will be detectable in the cases in between. The dotted line 180 ($Z_{focus}$) represents the focusing depth.

As illustrated in FIG. 9A, the OCT detection window 132 is also selected to position a reflection 192 of the posterior surface 127 of the patient interface lens 96 above the highest possible location of the anterior surface 129 of the cornea 122. This choice leaves the reflection 192 of the posterior patient interface lens surface 127 behind by 6 and is 6 from the closest the cornea 122 can be. Since the anterior cornea surface 129 is detected from above, the potential presence of the reflection 192 in the OCT detection window 132 does not interfere with the detection of the cornea anterior surface 129. The usable range of this OCT window is:

$$Z_{min} = 2*Zoct + \delta \quad \text{(marked as a dotted black line)}$$

$$Z_{max} = Zoct + R_{water} \quad \text{(to the end)}$$

$$Zoct_{actual}\,|_{CLp}(0,0) = (Zed_{actual}\,|_{CLp})\frac{2}{N_{water}}$$

The anterior surface 129 of the cornea 122 is computed by (plane fitting via) taking the median of the transformed pixel position of the surface points as:

A. Cornea Location =

$$Zoct_{actual}\,\bigg|_{CLp}(0,0) + \text{Median}\left[LUT_{Zed}(X, Y) + \frac{R_{water}*Pixel_n}{511}\right]$$

If the Cornea Anterior location is not found, assumed values used for a subsequent scan to locate points on the anterior surface 129 of the cornea 122 can be created at:

Cornea Location=Water Gap minimum

Cornea Focus=Water Gap Nominal

In many embodiments, the group of A-scans arranged as a spiral used to determine the z position of the anterior surface 129 of the cornea 122 uses two or more focus depths. For example, FIG. 9C shows an example group of A-scans 194 arranged as a spiral that can be used to locate the anterior surface 129 of the cornea 122. The A-scans 194 include five separate spiral patterns that are each focused at a different depth, with the focus depth of adjacent spiral patterns being separated by 0.5 mm. Any suitable number of different focus depths (e.g., 2, 3, 4, 5, 6, 7, 8 or more) can be used. Other suitable separation between focus depths of adjacent patterns (e.g., 0.25 mm, 0.4 mm, 0.6 mm, 0.75 mm) can also be used. By varying the focus depth, an increase in the resulting signal can be achieved by increasing the amount of radiation that is reflected from the structure being measured back to the OCT light source and detection device 98.

In many embodiments, the group of A-scans arranged as a spiral used to determine the z position of the anterior surface 129 of the cornea 122 is limited in transverse extent so as to limit the number of targeted locations and concentrate the targeted locations around the likely location of the apex of the anterior surface 129 of the cornea 122. For example, the group of A-scans arranged as a spiral used to determine the z position of the anterior surface can have a maximum transverse dimension of less than 2.0 mm. In a preferred embodiment, the group of A-scans arranged as a spiral used to determine the z position of the anterior surface can have a maximum transverse dimension of less than 1.2 mm (e.g., 1.0 mm as shown in FIG. 9C).

Edge Detection

Each A-scan of the OCT scan of the patient interface lens can be searched for the maximum brightness point. The identified maximums that are above a threshold can be used to define CLa and CLp.

As discussed herein, the Anterior Cornea prescan uses a series of small spiral scans with changing focus location as shown in FIG. 9C. A similar prescan approach can also be used to locate the anterior surface of the lens capsule 133 and to locate the posterior surface of the lens capsule 135.

Figure 10A:
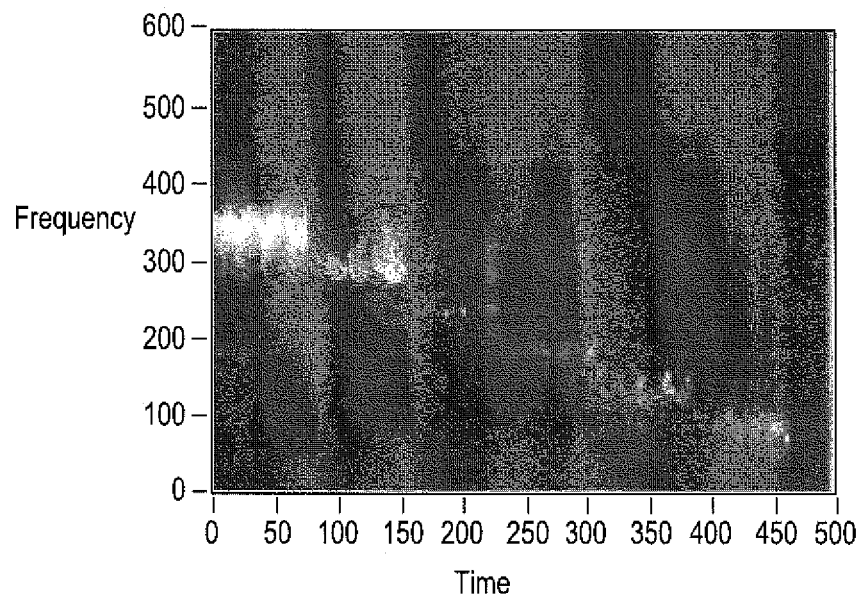
FIG. 10A illustrates OCT scan data generated using an OCT scan pattern having multiple focus depths, in accordance with many embodiments.
Figure 10B:
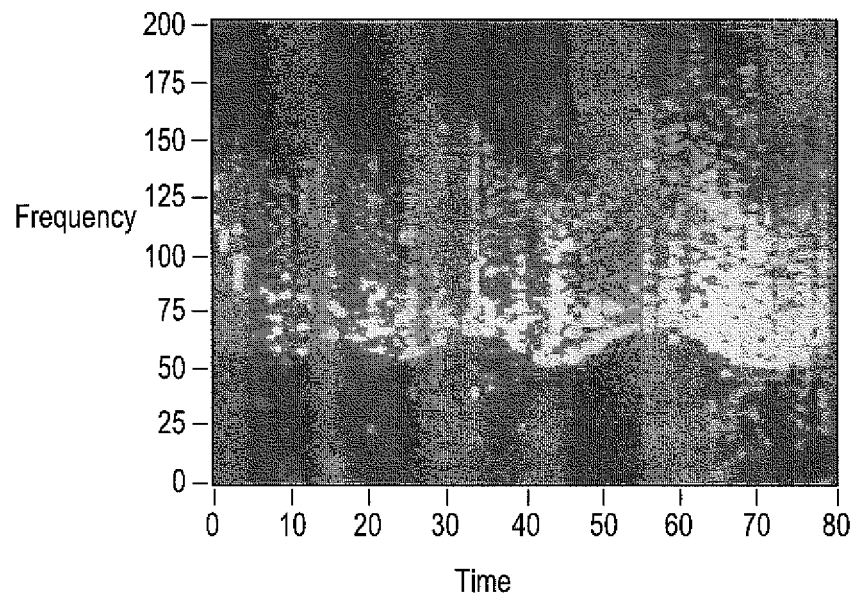
FIG. 10B shows a view of the OCT scan data of FIG. 10A for one of the focus depths.
Figure 10C:
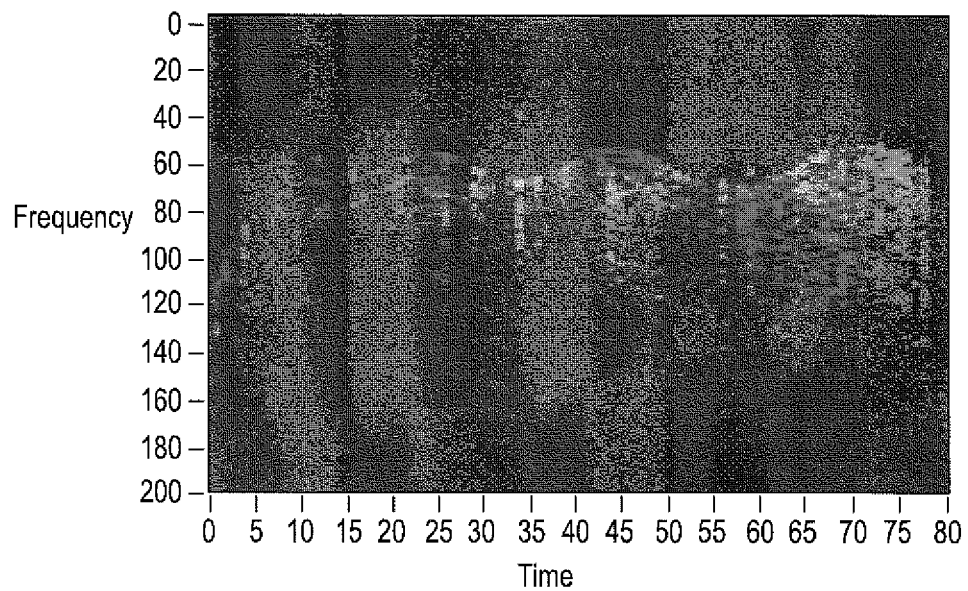
FIG. 10C shows original OCT scan data for one focus depth for the OCT scan data of FIG. 10A.
Figure 10D:
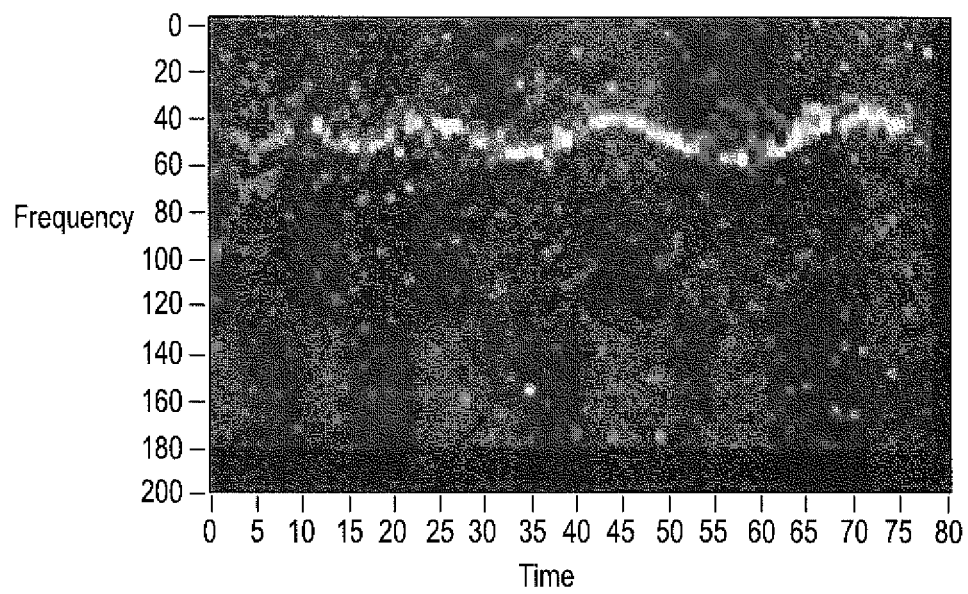
FIG. 10D shows a convoluted image with Gaussian derivative for the OCT scan data of FIG. 10A, in accordance with many embodiments.

In each of the focusing steps in a given prescan, a search for an edge within a suitable number of pixels from the focusing location can be performed. For example, Canny edge detection can be performed within every focusing step window to find edges. FIG. 10A shows OCT data depicting a stepping focus. FIG. 10B shows a view of the OCT data of FIG. 10A for one focus step. The Canny edge detection convolutes A-scans with a derivative of a Gaussian. The Kernel is generated using a Gaussian first derivative with standard deviation and a number of standard deviations. Edge candidates are the maximum or minimum within each convolution, but are only considered for surface fitting if they are in absolute value larger than a suitable threshold. FIG. 10C shows original OCT scan data for one focus. FIG. 10D shows a convoluted image with Gaussian derivative. And FIG. 10E shows a detected edge 196.

Cornea Scan

A group of A-scans arranged as a spiral can be commanded primarily to locate points on the anterior and posterior cornea surfaces 129, 131. The spiral can be focused between the two cornea surfaces, according to their nominal dimensions. A surface model (e.g., a sphere, an ellipsoid) of the anterior surface 129 of the cornea 122 can then be determined using points located on the anterior surface 129 of the cornea 122. The previously found location of the anterior surface 129 of the cornea 122 can also be used in the determination of the surface model of the anterior surface 129 of the cornea 122. A plane can be fit to the location of the posterior corneal surface 131. A surface model (e.g., a sphere, an ellipsoid) of the posterior surface 131 of the cornea 122 can be determined using the points located on the posterior surface of the cornea. The plane fit can also be used in the determination of the surface model of the posterior surface 131 of the cornea 122. As illustrated in FIGS. 11A through 11D, the Cornea Scan can be commanded with:

$$Zoct_{commanded}|_{CLp} = A. \text{ Cornea Location} - \delta$$

$$Zed_{commanded}|_{CLp} = (A. \text{ Cornea Location} - \delta)\frac{n_{water}}{2}$$

$$Zfocus|_{CLp} =$$
$$A. \text{ Cornea Focus} + \frac{\text{Cornea Thickness}_{nom}}{2} + R_{nom} - \sqrt{R_{nom}^2 - X^2 - Y^2}$$

$$LUT_{OCT\,ZI}(X, Y, Z_{focus}|_{CLp}, CLp) \rightarrow X_m, Y_m, Z_L$$

$$R_{nom} = \frac{A. \text{ Cornea Radius}_{nom} + P. \text{ Cornea Radius}_{nom}}{2}$$

Figure 11A:
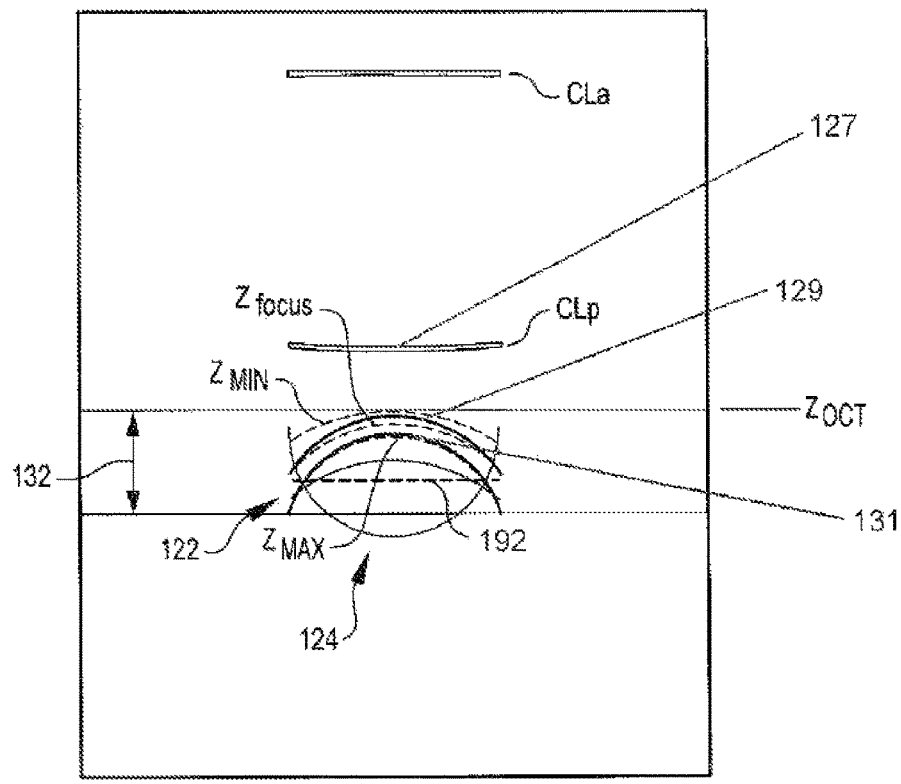
FIGS. 11A through 11D are simplified diagrams illustrating aspects of an OCT scan used to measure the spatial disposition of a cornea, in accordance with many embodiments.
Figure 11B:
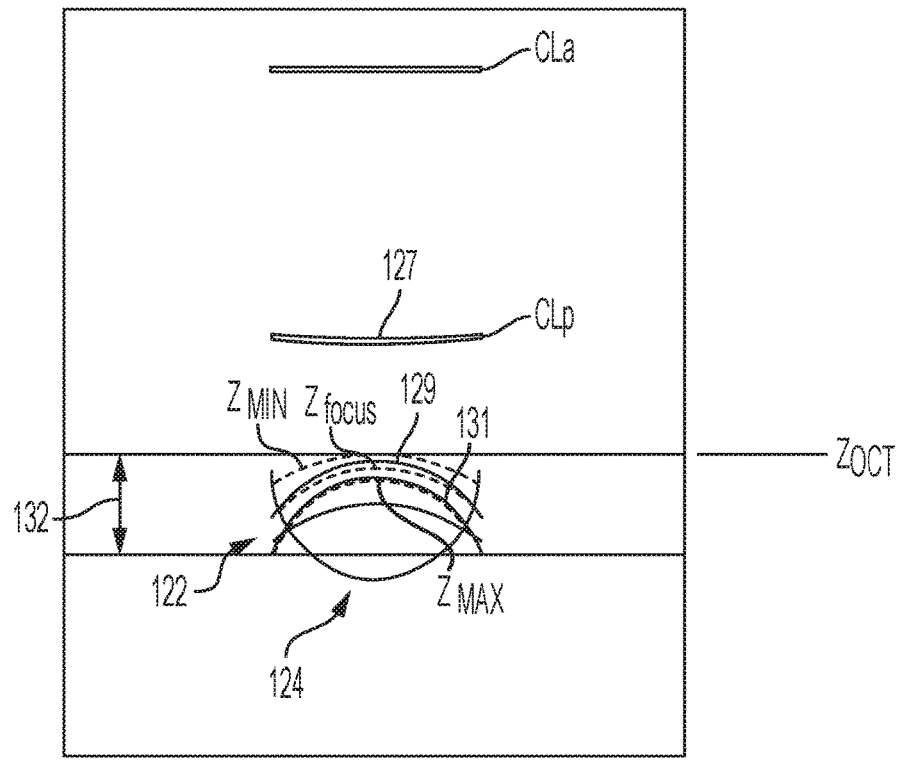
Figure 11C:
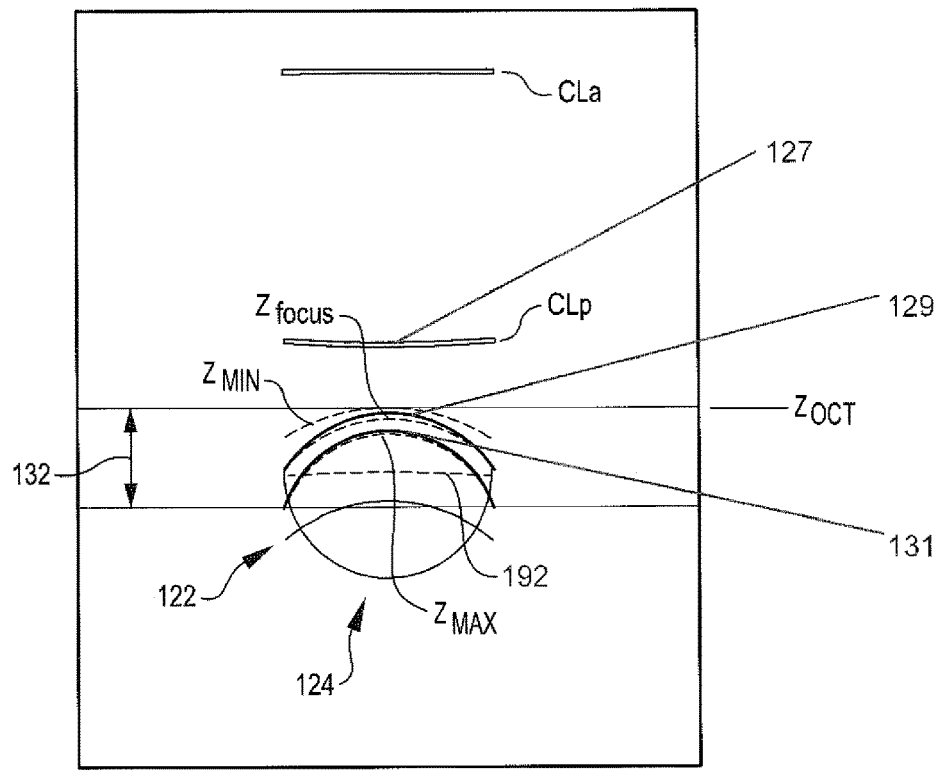
Figure 11D:
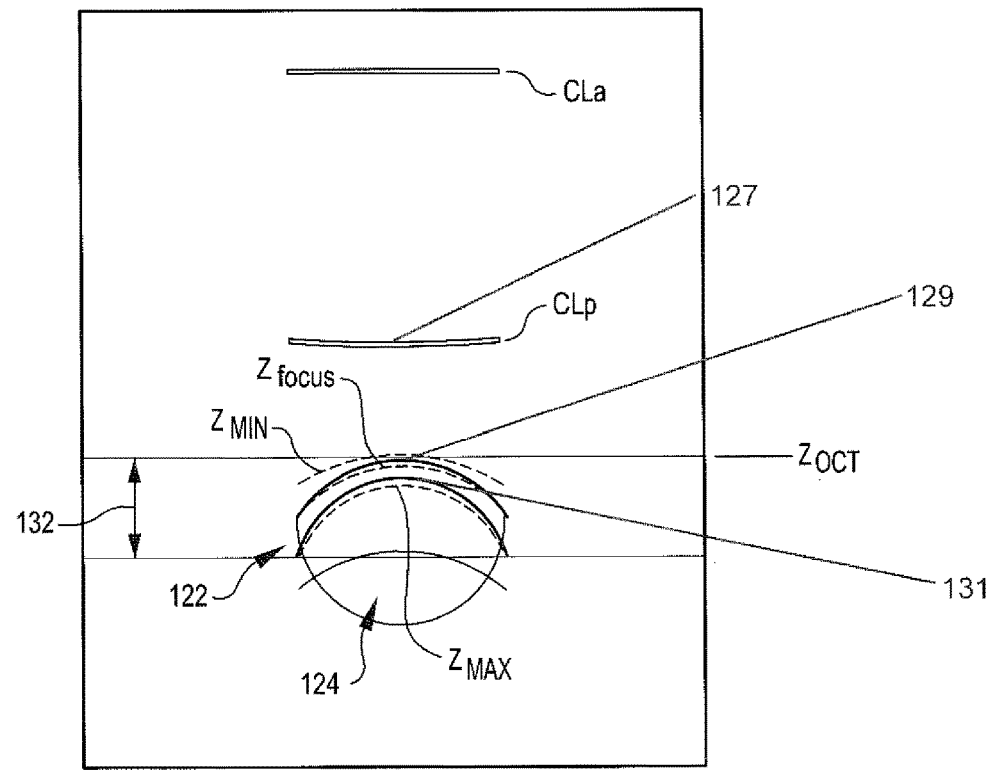

FIGS. 11A through 11D show combinations of maximum and minimum anterior chamber depth and gap between the posterior surface 127 of the patient interface lens and the patient's eye ("water gap"). FIG. 11A shows the minimum anterior chamber depth with the minimum water gap. FIG. 11B shows the minimum anterior chamber depth with the maximum water gap. FIG. 11C shows the maximum anterior chamber depth with the minimum water gap. FIG. 11D shows the maximum anterior chamber depth with the maximum water gap.

A portion of the OCT window can be processed so as to only look for the corneal anterior and posterior surfaces 129, 131 in likely locations. The processed portion of the OCT window can be located between an upper bounding surface (Zmin) and a lower bounding surface (Zmax). For example, the processed portion of the OCT window can be X and Y dependent such as:

$$Z_{min} = Zoct(X,Y) + R_{min} - \sqrt{R_{min}^2 - X^2 - Y^2}$$

$$Z_{max} = Zoct(X,Y) + \text{Cornea Thk}_{max} + \delta + R_{max} - \sqrt{R_{max}^2 - X^2 - Y^2}$$

$$R_{min} = A. \text{ Cornea Radius}_{max}$$

$$R_{max} = P. \text{ Cornea Radius}_{min}$$

The processed window is configured to encompass likely spatial distributions for the anterior and posterior cornea surfaces 129, 131. Each identified point on the surface of either the cornea anterior surface 129 or the cornea posterior surface 131 can be translated from the B-Scan image into Cartesian coordinates as:

$$\text{Point Coordinate } (X, Y)|_{CLp} =$$
$$(Zed_{actual}|_{CLp})\frac{2}{N_{water}} + \frac{R_{water} * Pixel_n}{511} + LUT_{Zed}(X, Y)$$

Anterior Lens Prescan

Figure 12A:
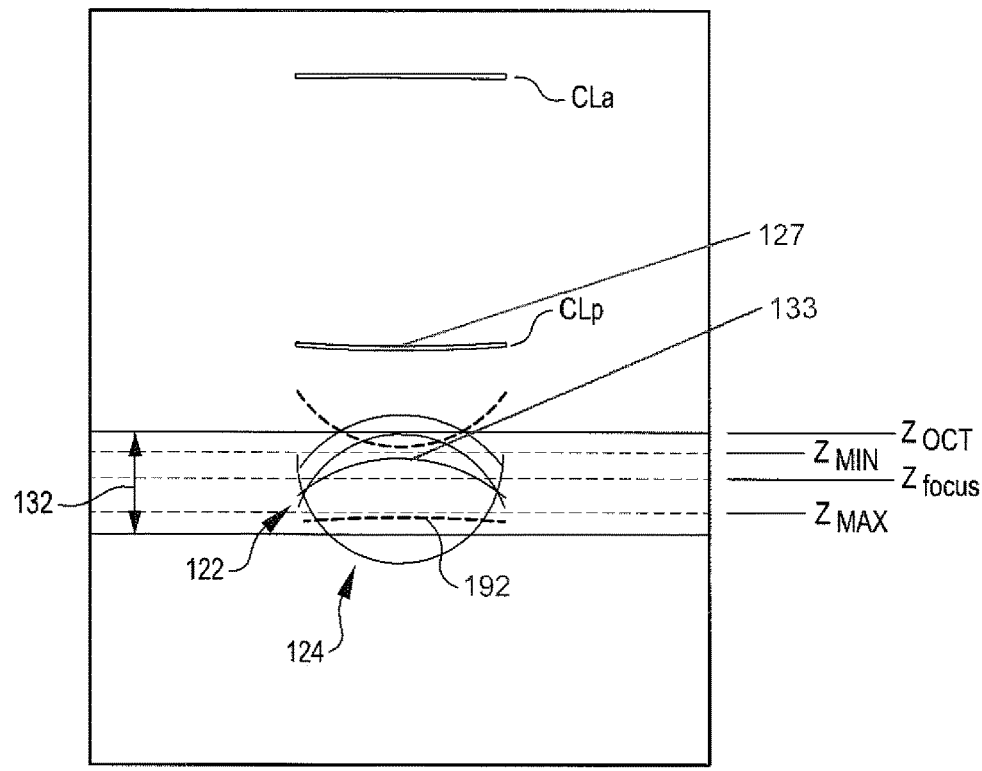
FIGS. 12A and 12B are simplified diagrams illustrating aspects of an OCT scan used to measure the location of an anterior surface of a lens, in accordance with many embodiments.
Figure 12B:
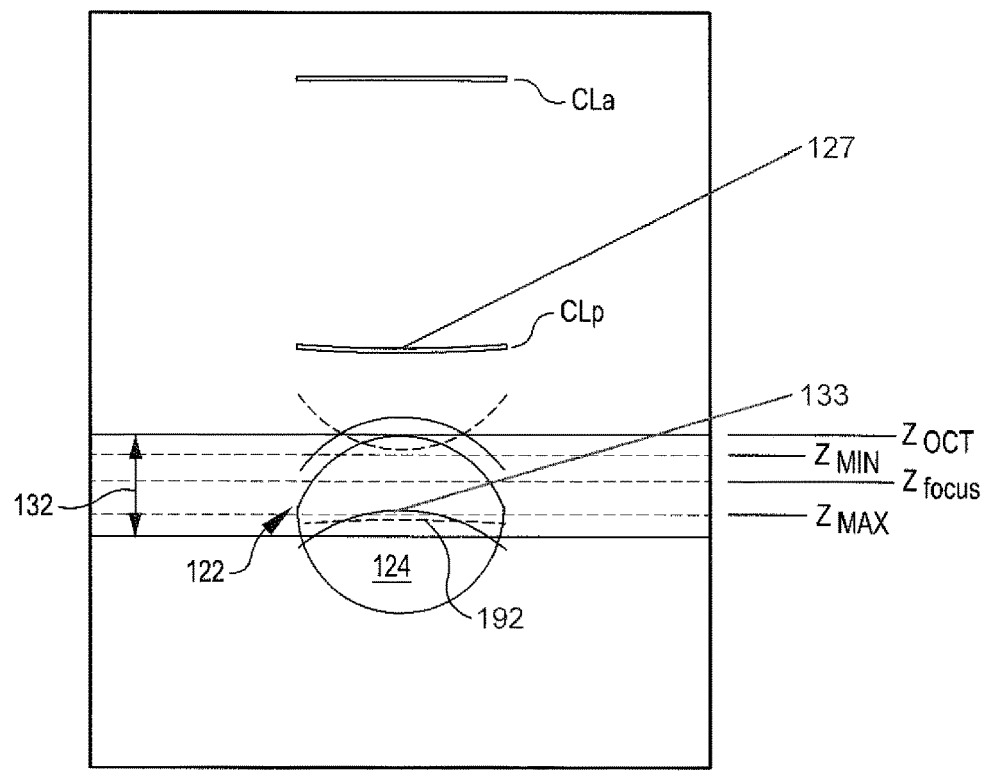

A group of A-scans arranged as a spiral can be commanded primarily to determine the location of the anterior lens surface 133. The group of A-scans used to determine the location of the anterior lens surface 133 can be focused at, for example, the nominal anterior chamber depth. A plane can be fit to the located anterior lens surface 133. As illustrated in FIGS. 12A and 12B, the group of A-scans used to determine the location of the anterior lens surface 133 can be commanded with:

$$Zoct_{commanded}|_{CLp} = A.\text{ Cornea Location} + \frac{\text{Anterior Chamber}_{min}}{2} - \delta$$

$$Zed_{commanded}|_{CLp} = \left(A.\text{ Cornea Location} + \frac{\text{Anterior Chamber}_{min}}{2} - \delta\right)\frac{n_{water}}{2}$$

$$Zfocus|_{CLp} = A.\text{ Cornea Location} + \text{Anterior Chamber}_{nom}$$

$$LUT_{OCT\,Zl}(X, Y, Zfocus|_{CLp}, CLp) \rightarrow X_m, Y_m, Z_L$$

FIGS. 12A and 12B illustrate minimum and maximum anterior chamber depth, respectively. To exclude reflections from the cornea 122 and the posterior surface 127 of the patient interface lens 96, the processed range of the OCT detection window can be set to be:

$$Z_{min} = A.\text{ Cornea Location} + \text{Anterior Chamber}_{nom} - \delta$$

$$Z_{max} = \text{Min}[2 * Zoct - \delta, Zoct + R_{water}]$$

The location of the Anterior Lens surface 133 can be calculated using:

$$A.\text{ Lens Location}|_{CLp} =$$
$$(Zed_{actual}|_{CLp})\frac{2}{N_{water}} + \frac{\sum_n\left\{LUT_{Zed}(X_n, Y_n) + \frac{R_{water} * Pixel_n}{511}\right\}}{n}$$

If the Anterior Lens surface 133 is not found, assumed values used for a subsequent scan to locate points on the anterior surface 133 of the lens 124 can be created at:

$A.$ Lens Location=$A.$ Cornea Location+Anterior Chamber minimum $A.$ Lens Focus=$A.$ Cornea Location+Anterior Chamber Nominal In many embodiments, the group of A-scans arranged as a spiral used to determine the z position of the anterior surface 133 of the lens 124 uses two or more focus depths. For example, the example group of A-scans 194 shown in FIG. 9C can also be used to locate the anterior surface 133 of the lens capsule. Variations discussed above with respect to the example group of A-scans 194 shown in FIG. 9C can also be applied with regard to the group of A-scans used to locate the anterior surface 133 of the lens capsule.

Anterior Lens Scan

Figure 13A:
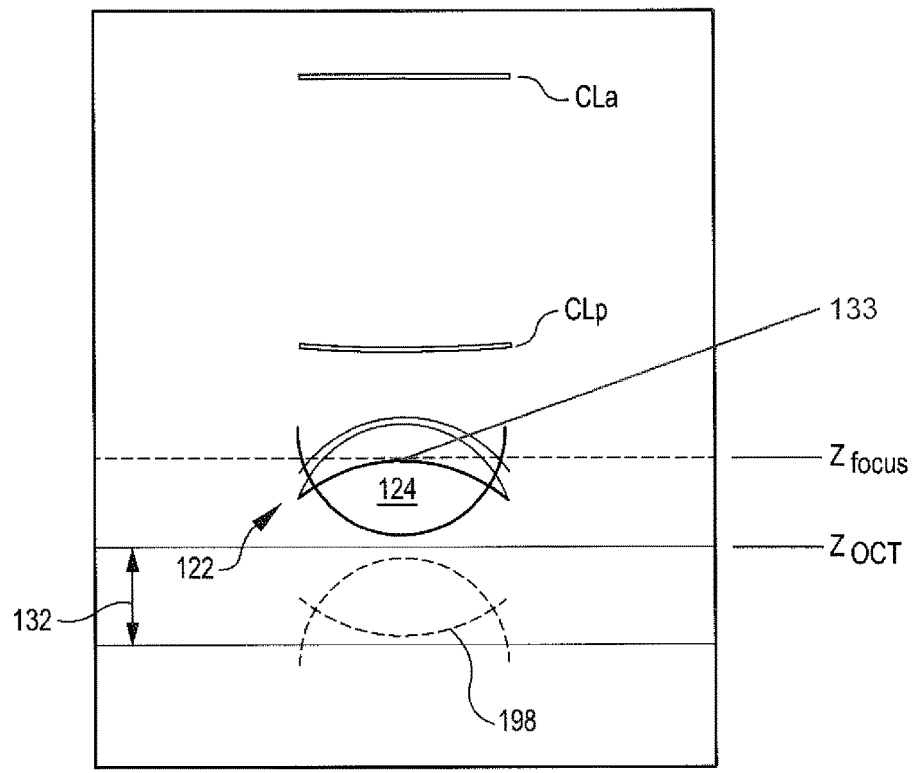
FIGS. 13A through 13D are simplified diagrams illustrating aspects of an OCT scan used to measure the spatial disposition of an anterior surface of a lens, in accordance with many embodiments.
Figure 13B:
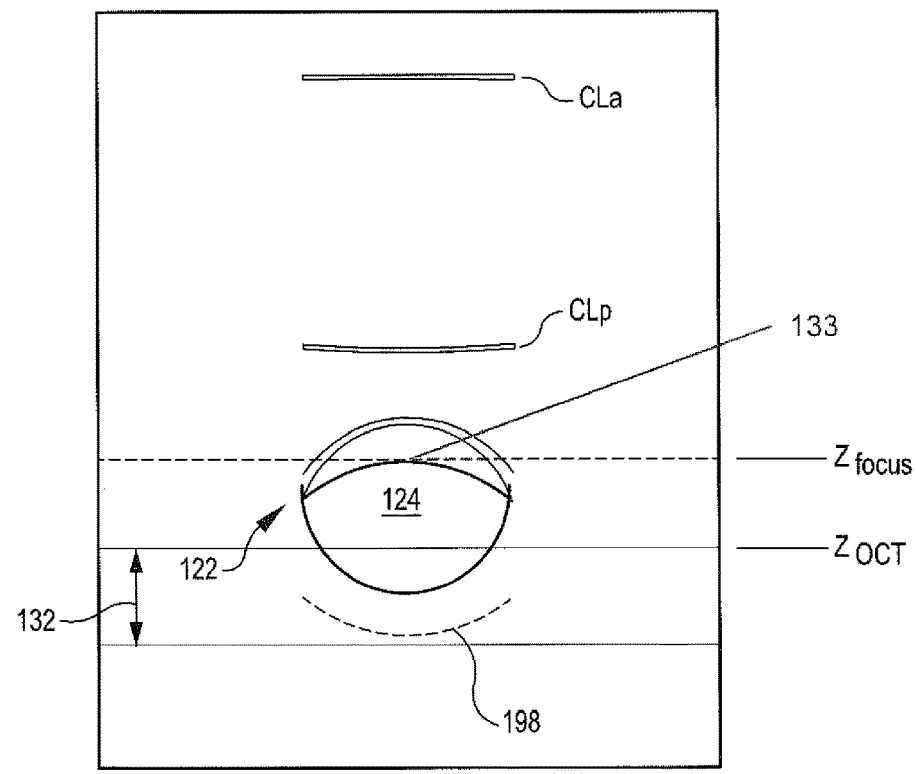

A group of A-scans arranged as a spiral can be commanded primarily to locate points on the anterior lens surfaces 133. The group of A-scans used to locate points on the anterior lens surface 133 can be focused, for example, at the nominal anterior chamber depth. As illustrated in FIGS. 13A and 13B, the group of A-scans used to locate points on the anterior lens surface 133 can be commanded with:

$$Zoct_{commanded}|_{CLp} = A.\text{ Lens Location}|_{CLp} + R_{water} - 6\delta$$

$$Zed_{commanded}|_{CLp} = (A.\text{ Lens Location}|_{CLp} + R_{water} - 6\delta)\frac{N_{water}}{2}$$

$$Zfocus|_{CLp} = A.\text{ Lens Focus}|_{CLp}$$

$$LUT_{OCT\,Zl}(X, Y, Zfocus|_{CLp}, CLp) \rightarrow X_m, Y_m, Z_L$$

Figure 13C:
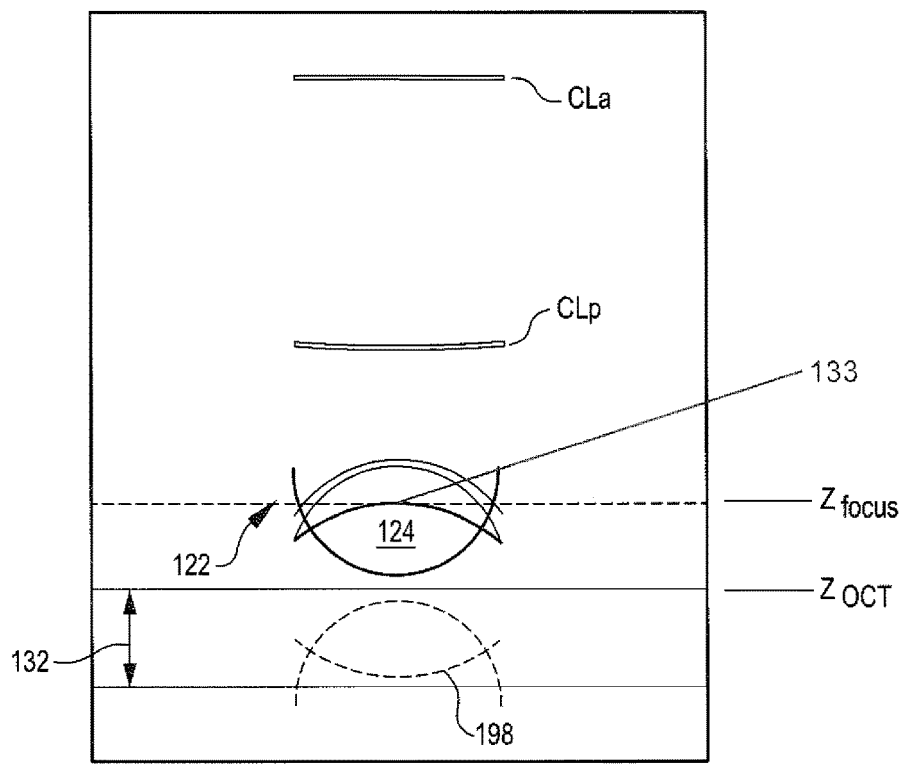
Figure 13D:
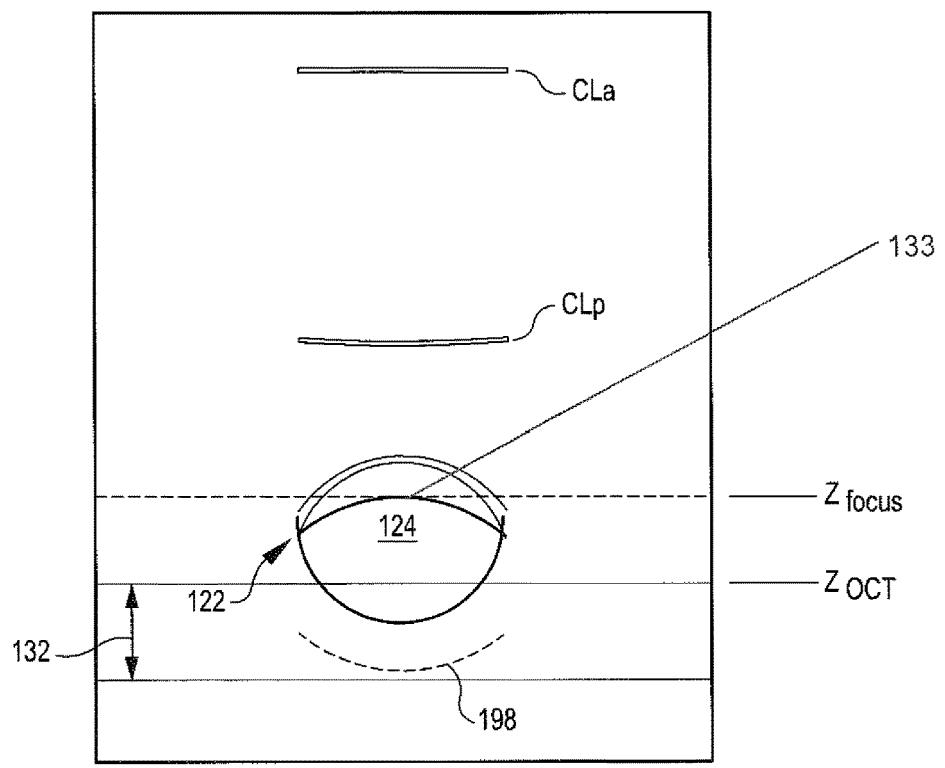

FIGS. 13A through 13D illustrate combinations of maximum and minimum anterior chamber depth and maximum and minimum lens thickness. FIG. 13A illustrates the minimum anterior chamber depth with the minimum lens thickness. FIG. 13B shows the minimum anterior chamber depth with the maximum lens thickness. FIG. 13C shows the maximum anterior chamber depth with the minimum lens thickness. FIG. 13D shows the maximum anterior chamber depth with the maximum lens thickness.

As illustrated in FIGS. 13A through 13D, the OCT detection window 132 is positioned below the anterior surface 133 of the lens capsule in all instances. Accordingly, the OCT data is processed to detect a lens anterior surface reflection 198.

Locations on the anterior surface 133 of the lens 124 can be calculated using the inverted scan.

$$\text{Point } A.\text{ Lens}|_{CLp}(X, Y) =$$
$$(Zed_{actual}|_{CLp})\frac{2}{N_{water}} - R_{water} + LUT_{Zed}(X_n, Y_n) + \frac{R_{water} * (511 - Pixel_n)}{511}$$

Note the media below the reflection of the anterior lens is water, so that no correction needs to take place.

Posterior Lens Prescan

Figure 14A:
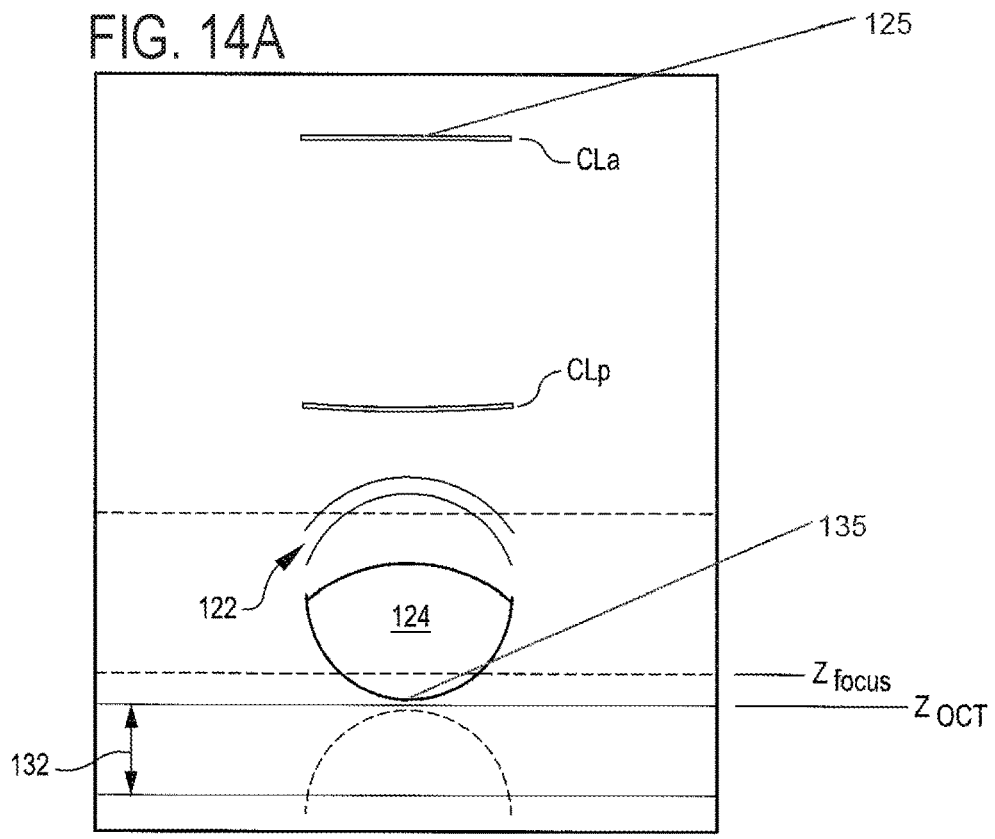
FIGS. 14A and 14B are simplified diagrams illustrating aspects of an OCT scan used to measure the location of a posterior surface of a lens, in accordance with many embodiments.
Figure 14B:
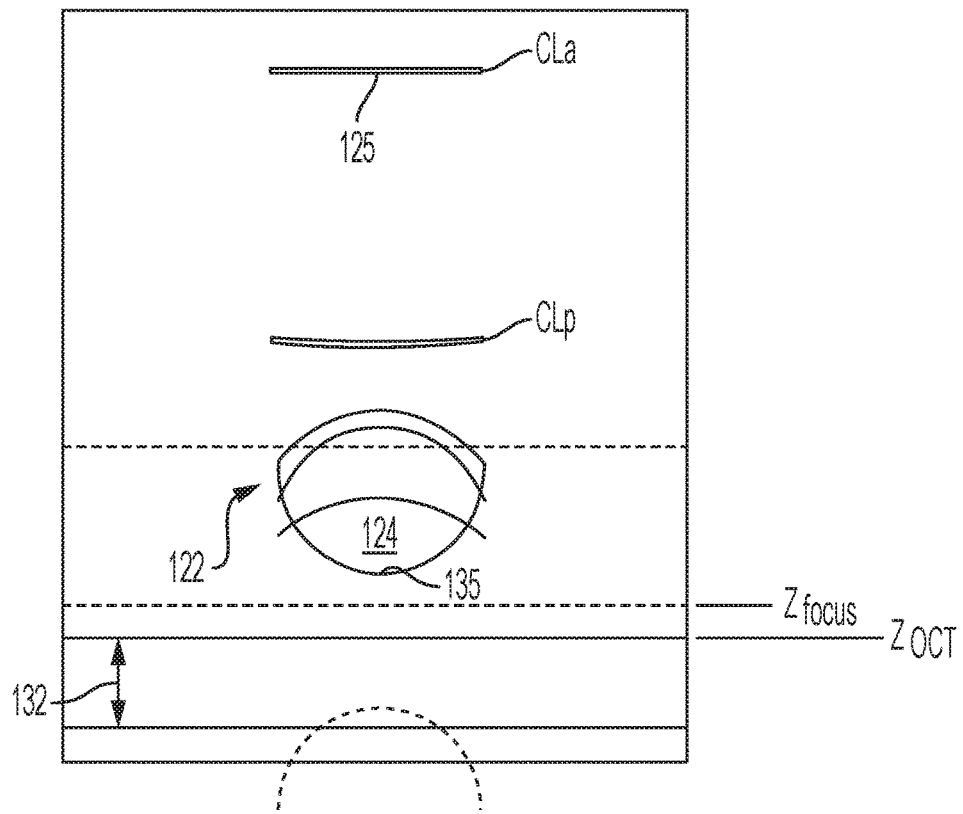

A group of A-scans arranged as a spiral can be commanded primarily to determine the location of the posterior lens surface 135. The group of A-scans used to determine the location of the posterior lens surface 135 can be focused below the located anterior surface 133 of the lens capsule by the nominal thickness of the lens 124. The location of the posterior lens surface 135 can be subsequently fitted with a plane. As illustrated in FIGS. 14A and 14B, the group of A-scans used to determine the location of the apex of the posterior lens surface 135 can be commanded with:

$$Zoct_{commanded}|_{CLp} =$$
$$A.\text{ Lens Location}\Big|_{CLp} + \text{Lens Thickness}_{max}\frac{N_{Lens-max}}{N_{water}} +$$
$$\delta + WG_{nom} + ACD_{nom} - WG_{min} - ACD_{min}$$

$$Zed_{commanded}|_{CLp} =$$
$$\left(A.\text{ Lens Location}\Big|_{CLp} + \text{Lens Thickness}_{max}\frac{N_{Lens-max}}{N_{water}} + \delta + WG_{nom} + ACD_{nom} - WG_{min} - ACD_{min}\right)\frac{N_{water}}{2}$$

-continued $$Zfocus\vert_{CLp} = A.\text{ Lens Location}\vert_{CLp} + \text{Lens Thickness}_{nom}\frac{N_{water}}{N_{Lens-nom}}$$

$$LUT_{OCT\ Zl}(X, Y, Zfocus\vert_{CLp}, CLp) \rightarrow X_m, Y_m, Z_L$$

FIGS. 14A and 14B illustrate minimum and maximum lens thickness, respectively. The OCT detection window 132 is located below the posterior surface 135 of the lens capsule in all instances so that the location of the posterior surface 135 of the lens capsule is determined using the inverted scan. Note that the reflection of the anterior surface 125 of the patient interface lens 96 is never in the scan window.

Location $P.\text{ Lens}\vert_{CLp}(X, Y) =$ $$A.\text{ lens } Loc + \left[\left\{(Zed_{actual}\vert_{CLp})\frac{2}{N_{water}} - R_{water}\right\} - A.\text{ lens } Loc\right]$$

$$\frac{N_{water}}{N_{Lens-max}} + \frac{\sum_n\left\{LUT_{Zed}(X_n, Y_n) + \frac{\frac{R_{air}}{N_{Lens-max}} \ast (511 - Pixel_n)}{511}\right\}}{n}$$

In many embodiments, the group of A-scans arranged as a spiral used to determine the location of the posterior surface 135 of the lens 124 uses two or more focus depths. For example, a group of A-scans similar to the example group of A-scans 194 shown in FIG. 9C can also be used to locate the posterior surface 135 of the lens capsule. Variations discussed above with respect to the example group of A-scans 194 can also be applied with regard to the group of A-scans used to locate the posterior surface 135 of the lens capsule.

Posterior Lens Scan

Figure 15:
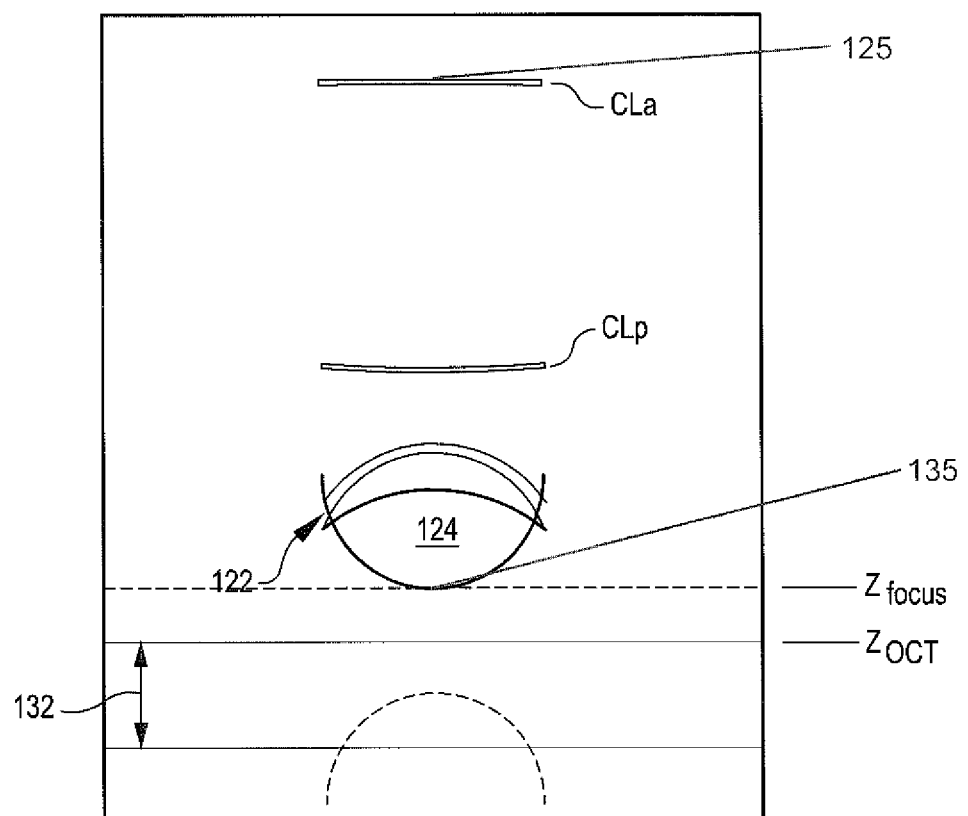
FIG. 15 is a simplified diagram illustrating aspects of an OCT scan used to measure the spatial disposition of a posterior surface of a lens, in accordance with many embodiments.

A group of A-scans arranged as a spiral can be commanded primarily to locate points on the posterior lens surface 135. The spiral can be focused at the depth of the posterior surface 135 of the lens capsule. As illustrated in FIG. 15, the scan can be commanded with the same OCT reference path length (same Zed) used to find the posterior lens surface location, but with a more precise focus:

$$Zoct_{commanded}\vert_{CLp} =$$

$$A.\text{ Lens Location}\vert_{CLp} + \text{Lens Thickness}_{max}\frac{N_{Lens-max}}{N_{water}} + \delta$$

$$Zed_{commanded}\vert_{CLp} =$$

$$\left(A.\text{ Lens Location}\vert_{CLp} + \text{Lens Thickness}_{max}\frac{N_{Lens-max}}{N_{water}} + \delta\right)\frac{N_{water}}{2}$$

$$Zfocus\vert_{CLp} = P.\text{ Lens Location}\vert_{CLp}$$

$$LUT_{OCT\ Zl}(X, Y, Zfocus\vert_{CLp}, CLp) \rightarrow X_m, Y_m, Z_L$$

FIG. 15 illustrates the OCT detection window 132 and the focus location ($Z_{focus}$) for the group of A-scans to locate points on the posterior lens surface 135. The OCT detection window 132 is located below the posterior surface 135 of the lens capsule in all instances so that locations on the posterior portion 135 of the lens capsule are determined using the inverted scan. Note that the reflection of the anterior surface 125 of the patient interface lens 96 is not in the scan window.

Point in $P.\text{ Lens}\vert_{CLp}(X, Y) =$ $$A.\text{ lens } Loc + \left[\left\{(Zed_{actual}\vert_{CLp})\frac{2}{N_{water}} - R_{water}\right\} - A.\text{ lens } Loc\right]$$

$$\frac{N_{water}}{N_{Lens-max}} + LUT_{Zed}(X_n, Y_n) + \frac{\frac{R_{air}}{N_{Lens-max}} \ast (511 - Pixel_n)}{511}$$

Automated Surface Fitting

In many embodiments, an iterative process is used to analyze the OCT scan data so as to automatically generate surface models for the cornea anterior surface 129, the cornea posterior surface 131, the lens anterior surface 133, and the lens posterior surface 135. The iterative process begins with identifying locations corresponding to a portion of the surface in question. Then, an initial surface model is generated based on the identified locations corresponding to a portion of the surface in question. Next, the initial surface model is used to identify regions of the OCT scan data to be searched for additional points on the surface in question. The identified additional points are then used to update the initial surface model. The iterative process continues until the surface model is finalized.

Figure 16A:
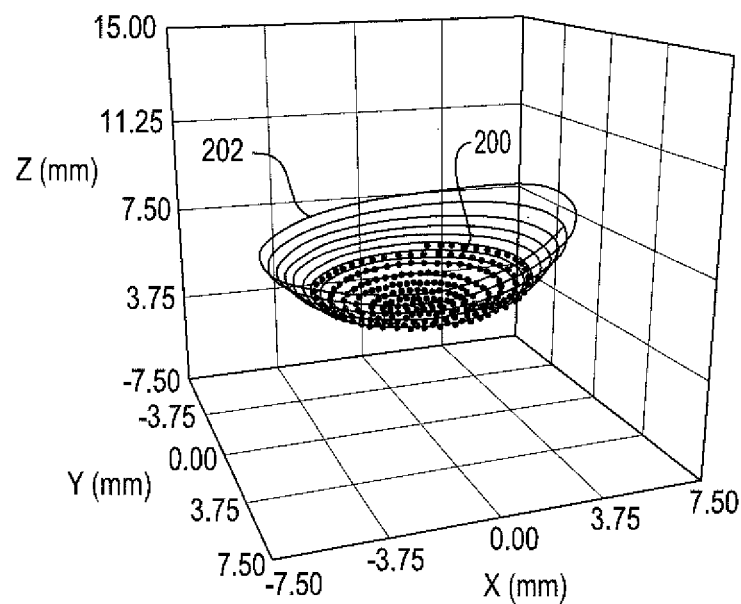
FIGS. 16A through 16D illustrate an iterative process for processing OCT scan data to identify locations on an optical surface, in accordance with many embodiments.
Figure 16B:
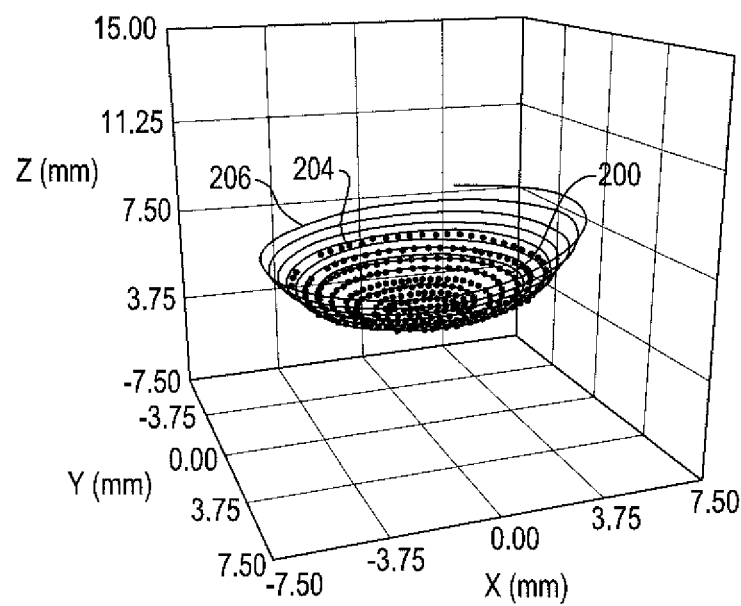
Figure 16C:
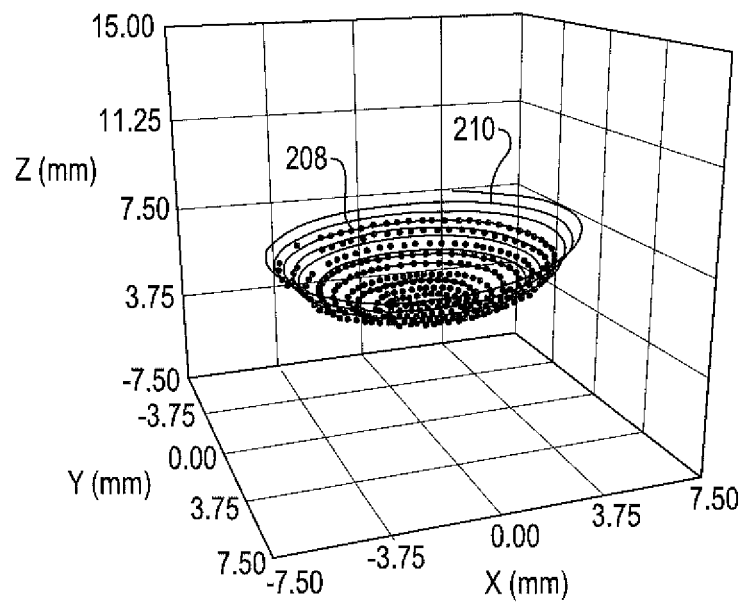
Figure 16D:
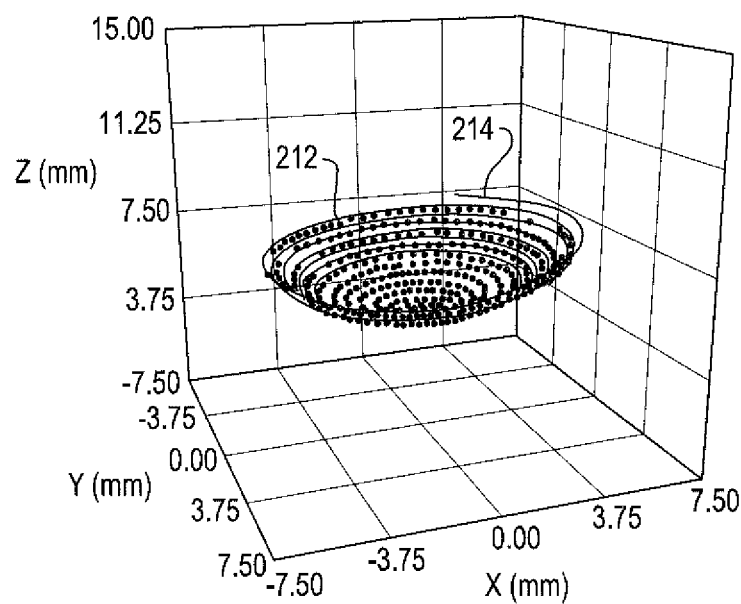

For example, FIGS. 16A through 16D illustrate an iterative process used to analyze the OCT scan data to automatically generate a surface model for the cornea anterior surface 129. The OCT scan that serves to image and construct the model of the anterior surface 129 of the cornea 122 can be focused using the location of the cornea anterior surface 129 identified by the cornea anterior prescan and statistical knowledge about the cornea anterior radius. A typical cornea anterior scan can contain in the vicinity of 1000 single A-scans (line scans). The iterative process to analyze the OCT scan data to construct the surface model of the cornea anterior surface 129 can start by segmenting a small number of the A-scans to detect a set of first locations on the cornea anterior surface 129. The identified location of the cornea anterior surface 129 and statistical knowledge of the cornea anterior radius can be used to identify a first portion of the OCT scan data to process to identify the first locations. As illustrated in FIG. 16A, the first locations 200 on the cornea anterior surface 129 can be used to construct a first surface model 202 (e.g., sphere, ellipsoid, conicoid, toroid, etc.) of the cornea anterior surface 129. The first surface model 202 can then be used to identify a second portion of the OCT scan data (a portion of the OCT scan data in which additional locations on the cornea anterior surface 129 are expected to be located based on the spatial distribution of the first model) to search for additional locations on the cornea anterior surface 129. For example, FIG. 16B illustrates a set of second locations 204 identified by searching the second portion of the OCT scan data. A second surface model 206 of the cornea anterior surface 129 can then be generated based on the location of the cornea anterior surface, the first locations 200, and the second locations 204. The second surface model 206 can then be used to identify a third portion of the OCT scan data (a portion of the scan data in which additional locations on the cornea anterior surface 129 are expected to be located based on the spatial distribution of the second model 206) to search for additional locations on the cornea anterior surface 129. For example, FIG. 16C illustrates a set of third locations 208 identified by searching the third portion of the OCT scan data. A third surface model 210 of the cornea anterior surface 129 can then be generated based on the location of the cornea anterior surface 129, the first locations 200, the second locations 204, and the third locations 208. The third surface model 210 can then be used to identify a fourth portion of the OCT scan data (a portion of the scan data in which additional locations on the cornea anterior surface 129 are expected to be located based on the spatial distribution of the third model) to search for additional locations on the cornea anterior surface 129. For example, FIG. 16D illustrates a set of fourth locations 212 identified by searching the fourth portion of the OCT scan data. A fourth surface model of the cornea anterior surface 129 can then be generated based on the location of the cornea anterior surface 129, the first locations 200, the second locations 204, the third locations 208, and the fourth locations 212. While the iterative process is described with four sets of iteratively identified locations, any suitable number of iterations can be used (e.g., 1, 2, 3, 4, 5, 6 or more). While any suitable surface model can be used (e.g., sphere, ellipsoid, conicoid, toroid, etc.), in a presently preferred embodiment, a specific ellipsoid is fitted to the locations identified by the iterative process. In a similar manner, the iterative process can be used to analyze the OCT scan data to automatically generate a surface model for the cornea posterior surface 133, the lens anterior surface 131, and/or the lens posterior surface 135.

Figure 17A:
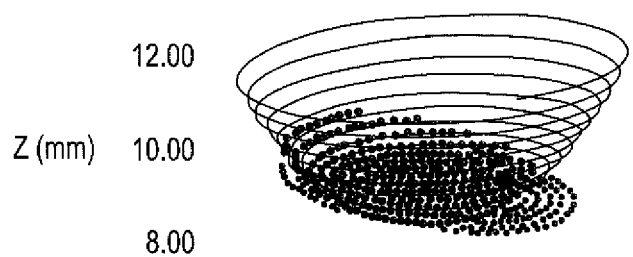
FIG. 17A illustrates OCT scan generated points used to generate a surface model of an iris, in accordance with many embodiments.
Figure 17B:
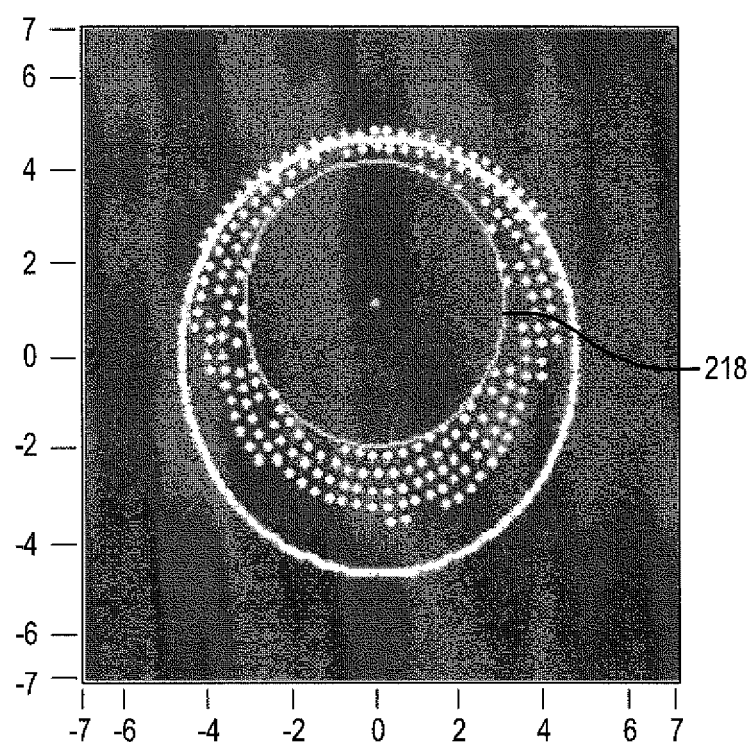
FIG. 17B illustrates pupil and limbus models generated based on the OCT scan generated iris points of FIG. 17A, in accordance with many embodiments.

A surface model of the iris can be generated using OCT edge points identified during processing of the OCT scan data to identify locations on the lens anterior surface 133. Specifically, identified OCT edge points that do not comply with the lens anterior surface model (such as points 216 shown in FIG. 17A) can be selected as potential locations on the iris for use in generating a surface model of the iris. For example, an oriented plane can be fit to the potential locations and the potential locations processed to identify a candidate pupil 218 (FIG. 17B) by determining the largest circle that can be fit inside the potential locations.

Figure 17C:
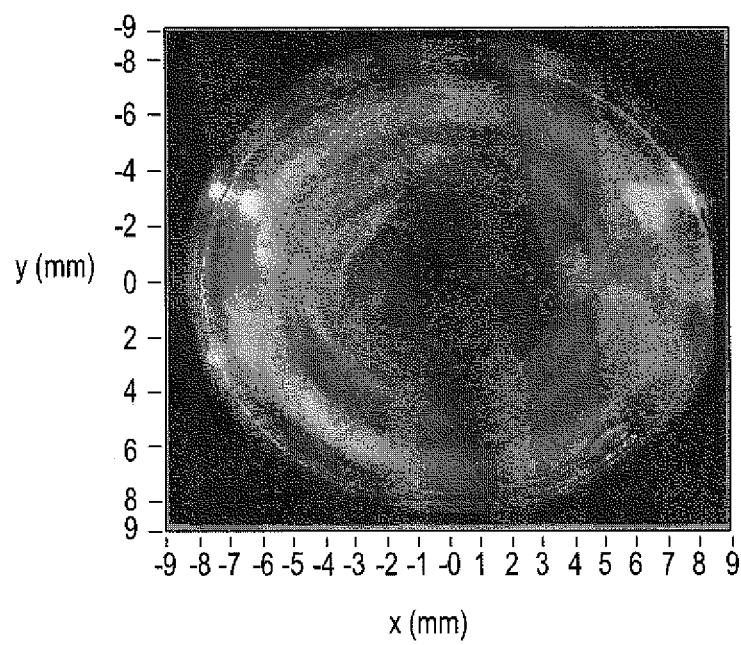
FIG. 17C shows pupil and limbus locations overlaid on a video image an eye, in accordance with many embodiments.

A video image (FIG. 17C) of the patient's eye 43 from the alignment guidance system 48 can also be processed either in isolation or using the OCT based iris plane and pupil. The video image can be searched for edges using a Canny filter. The search can proceed radially outward from the center of the OCT found pupil. Once edges are found, an outlier removal scheme can be implemented by sequentially fitting an ellipse specific to the pupil. Edges located away from the pupil can be removed.

Figure 17D:
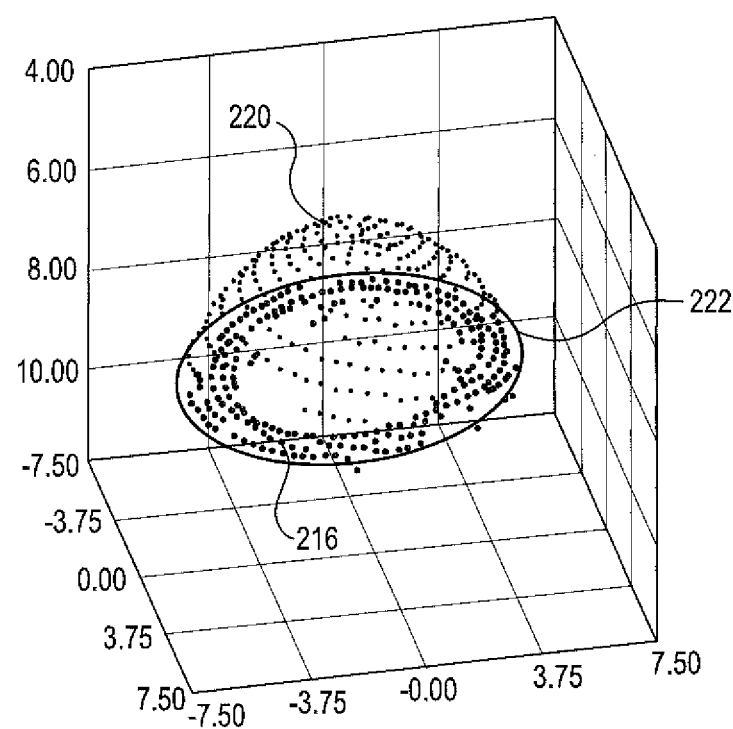
FIG. 17D shows cornea anterior surface locations, iris locations, and a curved-line model of the limbus generated by intersecting a cornea anterior surface model fit to the cornea anterior surface locations and the oriented plane fit to the iris locations, in accordance with many embodiments.

The location of the limbus of the patient's eye 43 can be approximated as the intersection between the cornea posterior surface model and the oriented plane fitted to the iris points. The projected view of this intersection is an ellipsoid in the x y plane. FIG. 17D shows cornea anterior surface locations 220, iris locations 216, and an intersection 222 of the cornea anterior surface model fit to the cornea anterior surface locations 220 and the oriented plane fit to the iris locations 216.

Composite Images

Figure 18A:
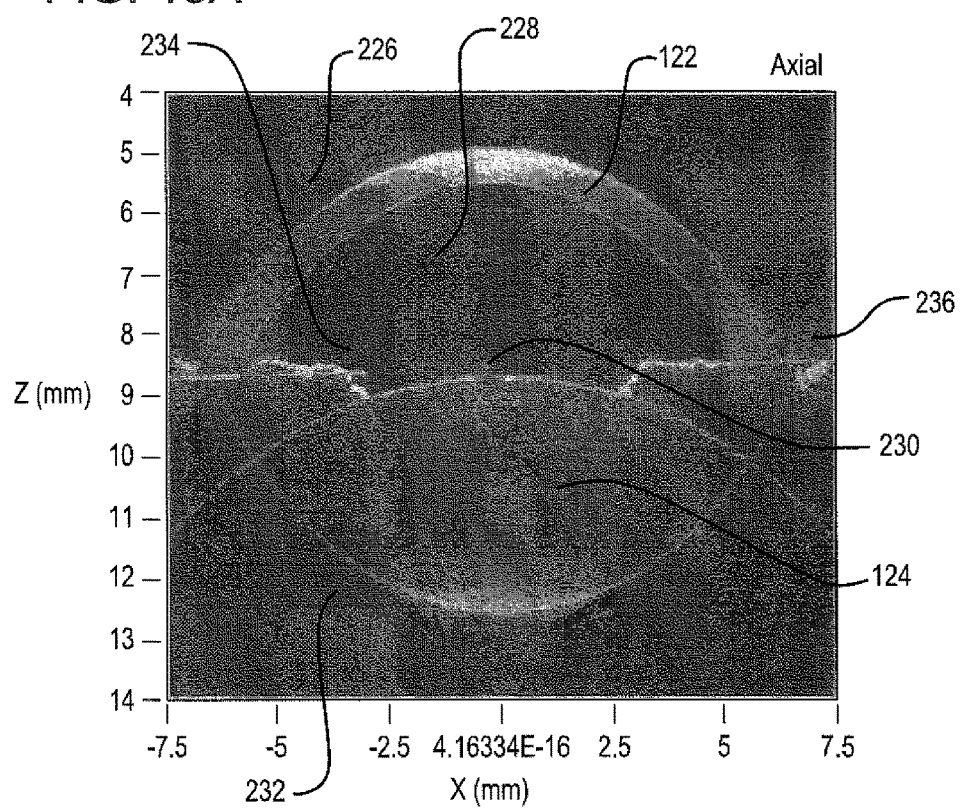
FIGS. 18A and 18B show axial and sagittal cross-sectional composite images of an eye, respectively, the composite images including cross-sections of surface models overlaid on OCT generated cross-sectional images of the eye, in accordance with many embodiments.
Figure 18B:
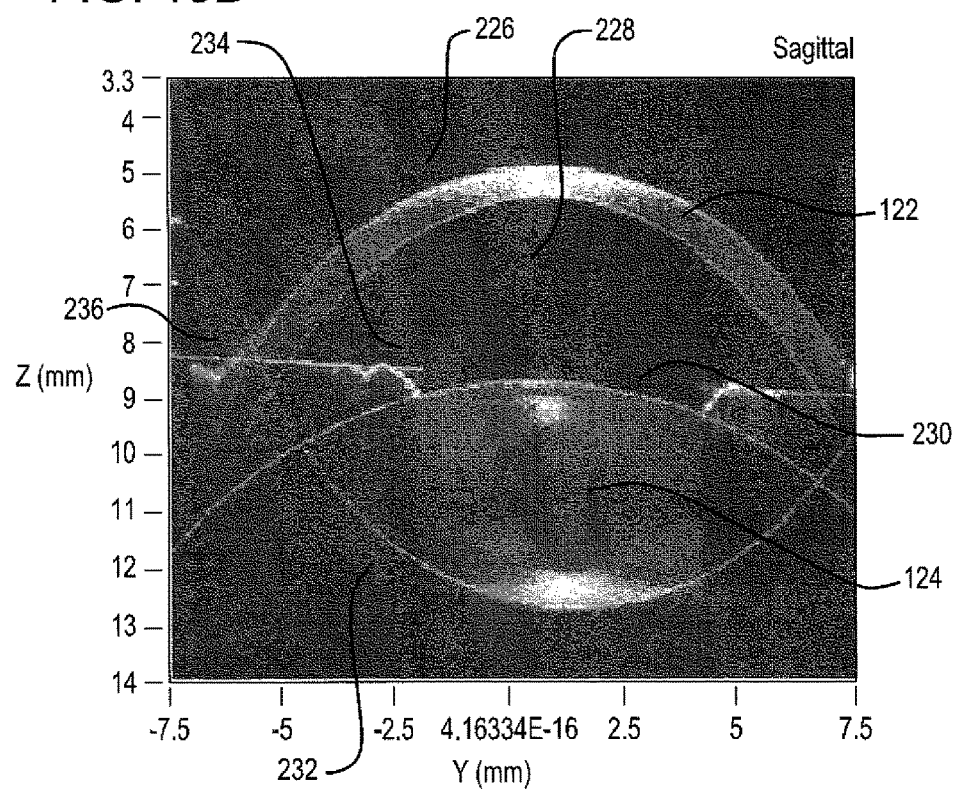

FIG. 18A shows an axial cross-sectional composite image of a patient's eye. FIG. 18B shows a corresponding sagittal cross-sectional composite image of a patient's eye. The composite images include OCT generated cross-sectional images of the cornea 122, the lens 124, and an iris 224. The composite images also include cross sections of surface models fit to the cornea 122, the lens 124, and the iris 224. The surface models include a cornea anterior surface model 226, a cornea posterior surface model 228, a lens anterior surface model 230, a lens posterior surface model 232, and an iris surface model 234. The intersection 236 between the cornea anterior surface model 226 and the iris surface model 234 can be used as to approximate the location of the limbus.

Optical Surface Verification

The optical surface models generated as described herein, as well as locations measured by the ranging subsystem 46 as described herein, can be checked relative to expected value ranges to identify when the optical surface model and/or the measured location falls outside of expected and/or allowable ranges. Such checking can be accomplished relative to the patient interface lens 96, the location of the cornea anterior surface 129, the cornea anterior and posterior surface models, the location of the lens anterior surface 133, the lens anterior surface model, the location of the lens posterior surface 135, the lens posterior surface model, and manual fits of the anterior and posterior surfaces of the cornea and of the lens.

Patient Interface Lens Checks

The computed posterior location of the patient interface lens and thickness can be compared to their nominal design dimension by the inequalities:

$$|CLp_{Computed} - CLp_{Nominal}| > CLp_{Tol}$$

$$|T_{computed} - T_{Nominal}| > T_{Tol}$$

If any of these inequalities is true, an error message can be sent and/or identification of the optical surfaces of the patient's eye 43 can be stopped. Suitable values for $CLp_{Nominal}$ (nominal location of the posterior surface of the patient interface lens 43), $CLp_{Tol}$ (allowable deviation of the location of the posterior surface of the patient interface lens 43), $T_{Nominal}$ (nominal thickness of the patient interface lens 43), and $T_{Tol}$ (allowable deviation of the thickness of the patient interface lens 43) can be used.

Cornea Anterior Surface Checks

The location of cornea anterior surface 129 can be checked relative to the treatment space Z axis to ensure that the location of the cornea anterior surface 129 is close to the treatment space Z axis and that the z location of the cornea anterior surface 129 is consistent with suitable maximum and minimum water gap values.

$$\sqrt{x_{center}^2 + y_{center}^2} \geq XY_{Tol} \text{ (e.g., 7.5 mm)}$$

$$\text{Not}(\text{Water Gap}_{min} \leq \text{Apex}_{Center\ A.\ cor.} \leq \text{Water Gap}_{max}.)$$

If any of these inequalities are true, a suitable error message can be sent and/or displayed and the cornea anterior location can be set to:

$$A.\ Cor_{Loc} = \text{Water Gap}_{min}.$$

$$A.\ Cor_{Loc\text{-}focus} = \text{Water Gap}_{nom}.$$

Cornea Anterior Surface Model Checks

The anterior cornea surface model (e.g., sphere) can be checked to ensure the x, y position of the center of the anterior cornea surface model is suitably close to the z-axis of the treatment space. The tolerance ($XY_{Tol}$) allows for some docking induced variation. If the following inequality is true, a suitable error message can be sent and/or displayed.

$$\sqrt{x_{center}^2 + y_{center}^2} > XY_{Tol} \text{ (e.g., 7.5 mm)}$$

The anterior cornea radius can be checked to make sure it is consistent with suitable minimum and maximum radius values. If the following condition is true, a suitable error message can be sent and/or displayed.

$$\text{Not}(R_{A.\ cor.\ min.} \leq R_{A.\ cor.} \leq R_{A.\ cor.\ max.})$$

The anterior cornea surface location can be checked to make sure it is consistent with suitable maximum and minimum water gap values. If the following inequality is true, a suitable error message can be sent and/or displayed.

Water Gap$_{min.}$≤$Z_{Center\ A.\ cor.}$−$R_{A.\ cor.}$≤Water Gap$_{max.}$

Cornea Posterior Surface Model Checks

The posterior cornea surface model can be checked to ensure the x, y position of the center of the posterior cornea surface model is suitably close to the center of the anterior cornea surface model. The tolerance (CXY$_{Tol}$) allows for some docking induced variation. If the following inequality is true, a suitable error message can be sent and/or displayed.

$\sqrt{(X_{A.Cor}-X_{P.Cor})^2+(Y_{A.Cor}-Y_{P.Cor})^2}$>CXY$_{Tol}$ (e.g.,7.5 mm)

A radius of the posterior cornea surface model can be checked to make sure it is consistent with suitable minimum and maximum radius values. If the following condition is true, a suitable error message can be sent and/or displayed.

Not($R_{P.\ cor.\ min.}$≤$R_{P.\ cor.}$≤$R_{P.\ cor.\ max.}$)

The thickness of the cornea 122 can be checked to make sure it is consistent with suitable maximum and minimum cornea thickness values. If the following inequality is true, a suitable error message can be sent and/or displayed.

Cornea Thickness$_{min.}$≤$Z_{Center\ A.\ cor.}$−$R_{A.\ cor.}$−A. Cornea$_{Apex}$≤Cornea Thickness$_{max.}$ Lens Anterior Surface Checks The location of the lens anterior surface 133 can be checked to ensure the x, y position of the lens anterior surface 133 is suitably close the z-axis of the treatment space and that the z location of the lens anterior surface 133 is consistent with the suitable maximum and minimum anterior chamber depth values and suitable maximum and minimum water gap values.

$\sqrt{x_{center}^2+y_{center}^2}$≥XY$_{Tol}$

Not(Water Gap$_{min.}$+Anterior Chamber$_{min.}$≤Apex$_{Center\ A.\ Lens.}$≤Water Gap$_{max.}$+Anterior Chamber$_{max.}$)

If any of the following conditions is true, a suitable error message can be sent and/or displayed and the inverted anterior lens scan can be placed and focused at A. Lens$_{Loc}$=A. Cor$_{Loc}$+Anterior Chamber$_{min.}$ A. Lens$_{Loc-focus}$=A. Cor$_{Loc}$+Anterior Chamber$_{max.}$ $Z_{OCT}$=A. Lens$_{Loc}$+$R_{OCT}$−δ (e.g.,$R_{OCT}$=4.87 mm,δ=1.5 mm)

$Z_{focus}$=A. Lens$_{Loc-focus}$+AD (e.g.,AD=0.25 mm)

Lens Anterior Surface Model Check

The lens anterior surface model can be checked to ensure the x, y position of the center of the lens anterior surface model is suitably close to the center of the cornea posterior surface model. If the following inequality is true, a suitable error message can be sent and/or displayed.

$\sqrt{(X_{A.Lens}-X_{A.Cor})^2+(Y_{A.Lens}-Y_{A.Cor})^2}$>CXY$_{Tol}$

The anterior lens radius can be checked to make sure it is consistent with suitable maximum and minimum radius values. If the following condition is true, a suitable error message can be sent and/or displayed.

Not($R_{A.\ lens.\ min.}$≤$R_{A.\ lens.}$≤$R_{A.\ lens.\ max.}$)

The location of the anterior lens surface can be checked to make sure it is consistent with suitable maximum and minimum anterior chamber depths. If the following condition is true, a suitable error message can be sent and/or displayed.

Not(A. Chamber$_{min.}$≤($Z_{Center\ A.\ lens.}$−$R_{Center\ A.\ lens.}$)−($Z_{Center\ A.\ Cor.}$−$R_{Center\ A.\ Cor.}$)≤A. Chamber$_{max.}$)

OCT Image Processing

Referring back to the assembly 62 illustrated in FIG. 3, in many embodiments, the OCT light source and detection device 98 employs spectral domain OCT (SDOCT). SDOCT is capable of high-resolution imaging at remarkably high speeds. Approaches for implementing SDOCT include spectrometer-based SDOCT and swept-source SDOCT. The spectral domain OCT may provide an optical path configured to perform an optical Fourier transform of the light reflected from the sample object. This Fourier transformed light signal is provided to the sensor array as Fourier domain signals measured with the detector. By digitally Fourier transforming the signals measured with the detector, the optical profile of light reflected from the beam path can be determined. This approach can allow the detector to measure several wavelengths simultaneously and allows rapid determination of the light intensity profile along the beam path from the tissue sample. However, as the detector measures the intensity of the optically Fourier transformed signal, the digital Fourier transform can produce artifacts in the images.

Figure 19:
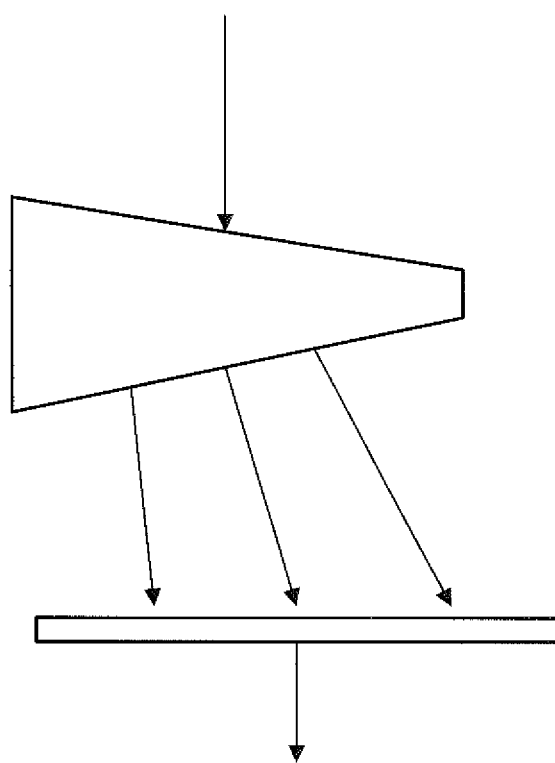
FIG. 19 is a simplified schematic diagram illustrating operating aspects of a spectrometer-based spectral domain OCT, in accordance with many embodiments.

In spectrometer-based SDOCT, a broadband light source is used to generate the light transmitted along the sample and reference paths and a spectrometer measures the resulting interference between the returning sample and reference light as a function of wavelength. The broadband light source can be, for example, a super-luminescent diode (SLD) or mode-locked laser. FIG. 19 is a simplified schematic diagram illustrating operating aspects of embodiments of the OCT light source and detection device 98. A spectral decomposer 238 separates and directs the superimposed returning sample and reference light 240 toward a photo-detector array 242 (e.g., a CCD sensor array or line scan sensor) in order to separate the detected light based on wavelength. The spectral decomposer 238 may comprise one or more of many components, and may comprise, for example, an optical grating, a prism, or equivalent. In many embodiments, the spectral decomposer comprises one or lenses introduced into the optical path, in order to focus the spectrally dispersed light on the sensor array, for example. The separated light 244 is incident upon sensors of the photo-detector array 242. The sensors of the photo-detector array 242 are distributed such that each sensor of the photo-detector array 242 receives a corresponding portion of the separated light 244 for corresponding wavelengths. The data of the senor array can be Fourier transformed to provide an intensity profile of light reflected back from the tissue along the beam path. The intensity profile obtained from the Fourier transform of the sensor scan can be referred to as an A-scan. In many embodiments, the resulting spectral data 246 generated by the photo-detector array 242 is rescaled and resampled evenly in k-space, before it is digitally Fourier transformed to get a depth profile of the imaged sample. A series of A-scans can be combined to produce a B-scan, which can, for example, be a cross-sectional depth profile of the imaged sample.

In swept-source SDOCT, a narrowband light source and a photo detector are employed to measure the resulting interference between the sample and reference light at different wavelengths over time. A swept-source SDOCT system can employ a rapidly tunable narrowband laser. In many embodiments, the output of the narrowband light source is swept linearly over a total optical bandwidth over a total sweep time and an interference signal is acquired at evenly spaced wave lengths. The interference signal can be acquired using a single detector or dual balanced detectors to compensate for intensity fluctuations. As the interference signal is acquired at evenly spaced wavelengths, the interference signal can be discrete Fourier transformed (DFT) directly to derive a depth-resolved OCT line scan of the tissue sample being imaged. Additional details of SDOCT imaging are described in the paper by Zahid Yoqoob, Jigang Wu, and Changhuei Yang, "Spectral domain optical coherence tomography: a better OCT imaging strategy", pages 6-13 in Molecular Imaging, December 2005.

Mirror Image Artifacts

Because the spectrum acquired in both spectrometer-based SDOCT and swept-source SDOCT is a real function, its Fourier transform (FT) is symmetrical with respect to the equal path-length line in the sample being imaged. The symmetrical nature of FT produces a mirror image artifact in the resulting image. As the photodetector can measure intensity of the interfering light but not the phase, the signal from the detector is positive for both positive and negative phase variations. For each A-scan of the image, there exists a location of the A-scan corresponding to the physical location of the tissue at which the light reflected from the mirror and the tissue have the same optical path length. As this location exits for each of the A-scans of the image, the A-scan images define an equal-path length line of the image. Without knowing the phase difference between the returning sample and reference light, Fourier-domain detection cannot distinguish positive and negative time delays and therefore produces an OCT image that is symmetrical about the equal path-length line. The symmetrical OCT image shows the corresponding uncertainty as to whether the image structure is actually disposed anterior to or posterior to the equal path-length line.

Figure 20:
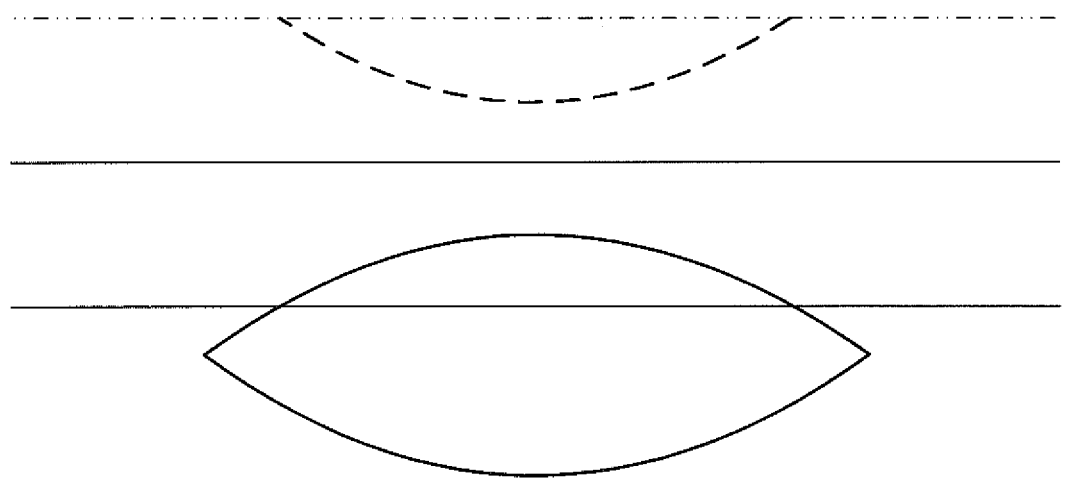
FIGS. 20 and 21 are simplified schematic diagrams illustrating generation of a mirror image artifact, in accordance with many embodiments.
Figure 21:
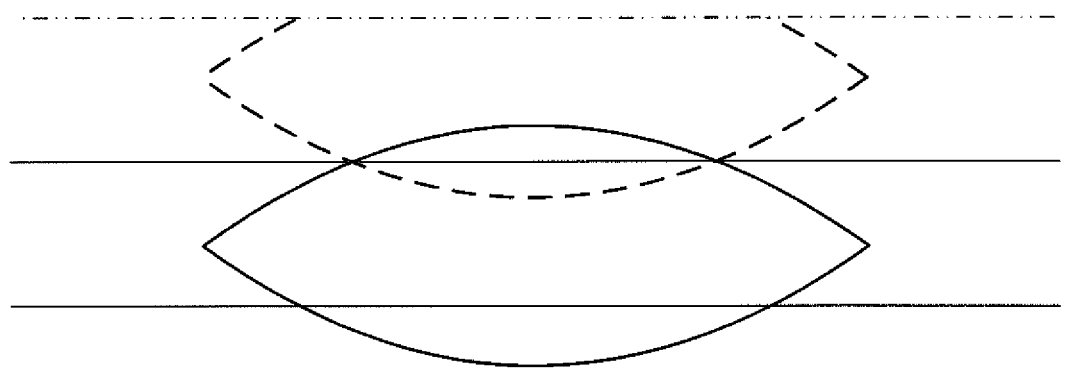

Referring now to FIG. 20 and FIG. 21, the generation of mirror image artifacts for a lens capsule 248 is illustrated for different physical locations of the lens capsule in relation to the equal path-length line of the OCT measurement system. The equal path-length line is designated as Zoct in each of the figures. In FIG. 20, Zoct is disposed anterior to and does not intersect the lens capsule 248 such that an imaged portion of the lens capsule 248 is disposed within the detection window 132. As a result, when sample light from the OCT light source and detection device 98 is reflected from the imaged portion of the lens capsule 248, the Fourier-domain detection employed generates an image that includes the imaged portion of the lens capsule 248 and a mirror image 250 of the imaged portion of the lens capsule 248. As the measured location of the imaged portion of the lens capsule 248 relative to Zoct is based on the resulting interference between the returning sample and reference light portions, and the resulting interference is a result of time-delay generated phase differences between the returning sample and reference light portions, the imaged portion of the lens capsule 248 and the mirror image 250 are symmetrical about the equal path-length line (Zoct). In the situation illustrated in FIG. 20, where the imaged structure of interest is contained solely on one side of the equal path-length line (Zoct), one side of the resulting image can truncated (in this case the top half containing the mirror image 250), thereby leaving the remaining half for image display.

In FIG. 21, the ZED stage and reference mirror of the OCT system are configured such that Zoct is located so as to intersect the lens capsule 248. Accordingly, the generated mirror image 250 crosses the equal path-length line (Zoct) and therefore is partially disposed in each of the two sides of the resulting image. As such, mere truncation of one side of the resulting image is insufficient to prevent the display of all of the mirror image 250.

Mirror image artifacts can be suppressed by, for example, measuring the spectral phase between the returning sample and reference path light and obtaining the complex scattered field whose inverse Fourier transform generates an image of the imaged structure without generating a mirror image artifact. The measured spectral phase indicates the side of the equal path-length line that the imaged structure is disposed. Such approaches for suppressing mirror image artifacts are described in: (1) Erich Gotzinger, Michael Pircher, Rainer A. Leitgeb, and Christoph K. Hitzenberger, "High speed full range complex spectral domain optical coherence tomography", Opt Express. 2005 Jan. 24; 13(2): 583-594; (2) Fercher A F, Leitgeb R, Hitzenberger C K, Sattmann H, Wojtkowski M. Complex spectral interferometry OCT. Proc. SPIE. 1999; 3564:173-178; (3) Wojtkowski M, Kowalczyk A, Leitgeb R, Fercher A F. Full range complex spectral optical coherence tomography technique in eye imaging. Opt. Lett. 2002; 27:1415-1417. [PubMed: 18026464]; and (4) Targowski P, Wojtkowski M, Kowalczyk A, Bajraszewski T, Szkulmowski M, Gorczynska I. Complex spectral OCT in human eye imaging in vivo. Opt. Commun. 2004; 229:79-84.

Figure 22:
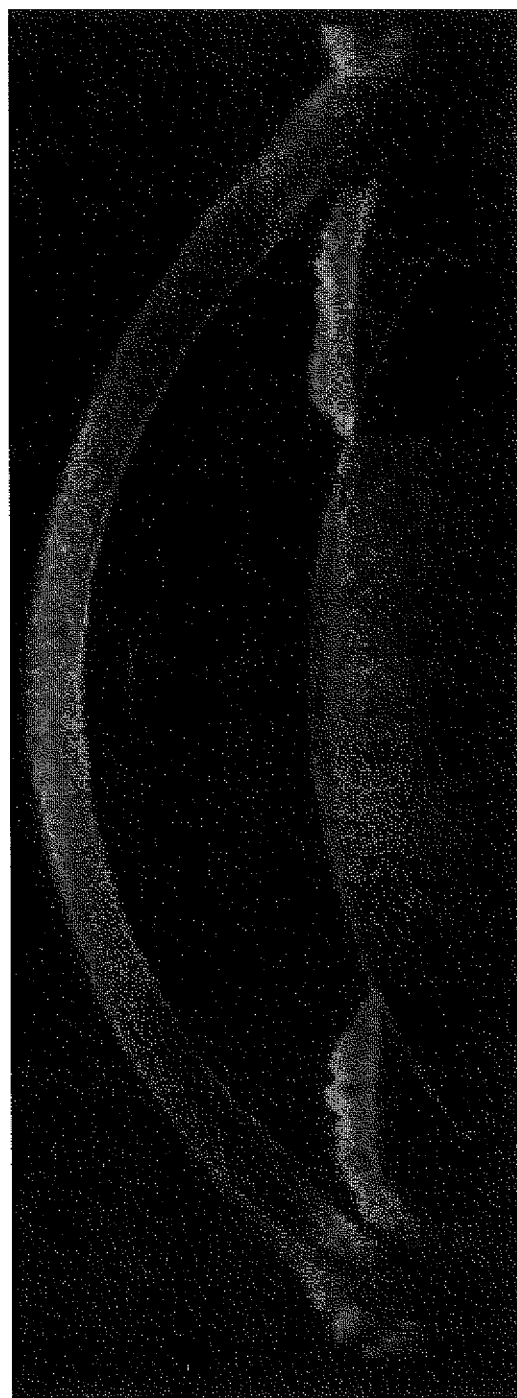
FIG. 22 shows a composite image of imaged structures of an eye, in accordance with many embodiments.

FIG. 22 shows a composite cross-sectional image 252 of an eye that was assembled from a plurality of A-scans with a range of equal path-length line (Zoct) locations. Suppression of mirror image artifacts was used to generate the composite cross-sectional image 252.

OCT Integration

In the embodiments of the laser eye surgery system 2 illustrated in FIG. 2, the ranging subsystem 46 images the eye 43 through both the shared optics 50 and the patient interface 52. The ranging subsystem 46, however, can be integrated into the laser eye surgery system 2 in any suitable manner.

Figure 23:
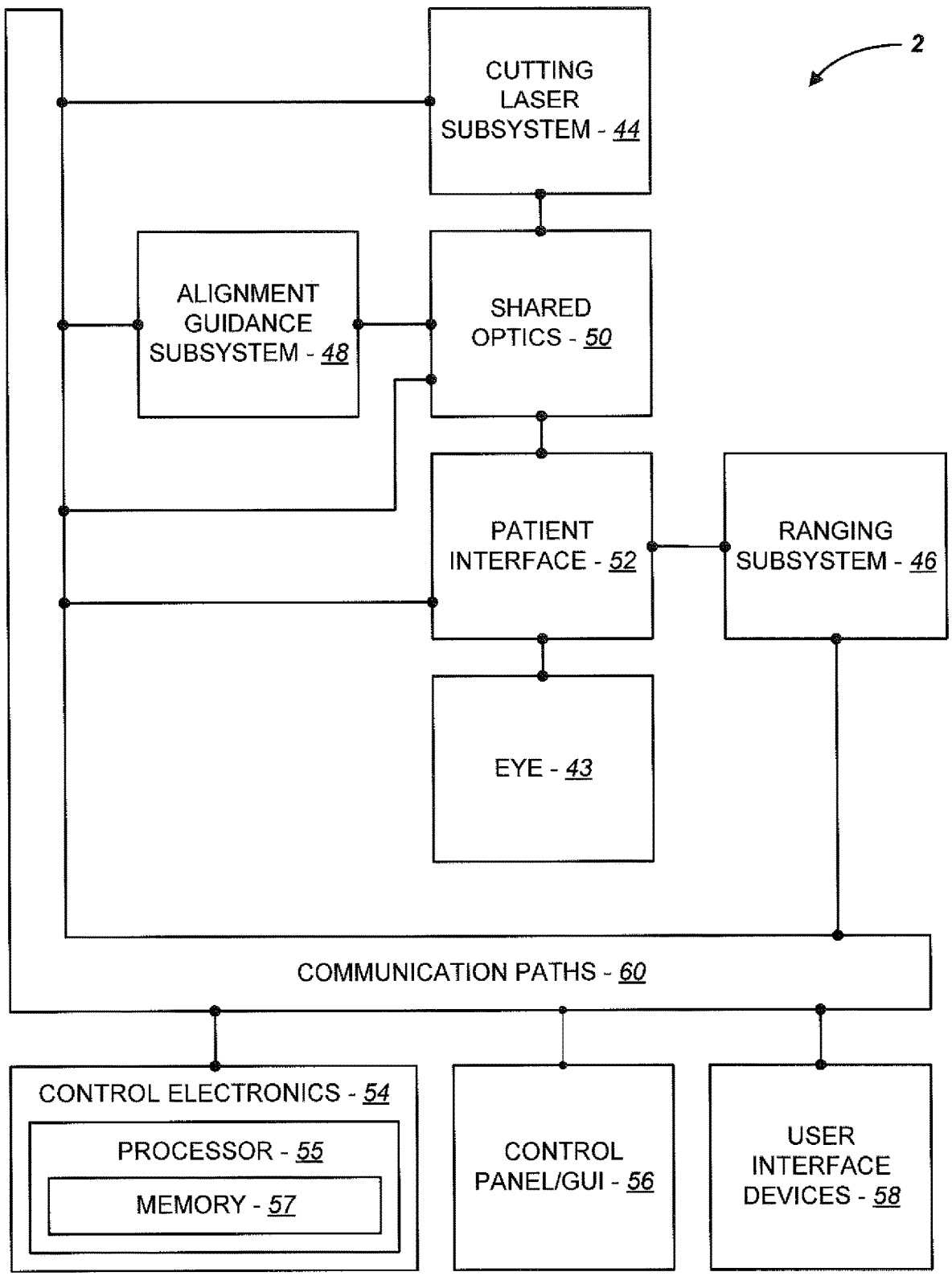
FIG. 23 is a simplified block diagram showing a top level view of an alternate configuration of the laser eye surgery system, in accordance with many embodiments.

Referring to FIG. 23, the ranging subsystem 46 can be integrated into the laser eye surgery system 2 downstream of the shared optics 50 so as to image the eye 43 through the patient interface 52. As another example, the ranging subsystem 46 can be integrated into the laser eye surgery system 2 so as to not image the eye 43 through the patient interface 52, but can, for example, image the eye 43 through a separate dedicated patient interface. In many suitable embodiments of the laser eye surgery system 2, the ranging subsystem 46 has a known or determinable spatial disposition(s) relative to the eye 43, thereby allowing the spatial disposition of eye structures measured by the ranging subsystem 46 to be used to accurately direct the laser pulse beam 66 to treat targeted eye structure(s).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A laser eye surgery system having an imaging system for generating a surface model of an optical surface of an eye, the eye including a cornea having anterior and posterior surfaces, a lens capsule having anterior and posterior surfaces, an iris, and a limbus, the method comprising:
a cutting laser subsystem configured to generate a pulsed laser beam;
an optical coherence tomography (OCT) imaging subsystem, the OCT imaging subsystem including an adjustable reference path length, the OCT imaging subsystem configured to produce a detection beam having a plurality of wavelengths such that the detection window spans a range of distances relative to the laser eye surgery system; and
control optics operably connected to the cutting laser subsystem and the OCT imaging subsystem, the control electronics programmed to:
generate an OCT sample beam;
process returning portions of the sample beam to locate a point on the optical surface relative to the laser eye surgery system;
focus the OCT sample beam within the eye with the length of the reference path set to position the detection window based on the location of the point on the optical surface such that the detection window encompasses the optical surface for all expected variations in spatial disposition of the optical surface;
process returning portions of the sample beam so as to detect first locations on the optical surface within a first radial distance of the point on the optical surface;
generate a first surface model of the optical surface based on the location of the point on the optical surface and the first locations on the optical surface;
process returning portions of the sample beam so as to detect second locations on the optical surface beyond the first radial distance and within a second radial distance from the point on the optical surface; and
generate a second surface model of the optical surface based on the location of the point on the optical surface and the first and second locations on the optical surface.

2. The system of claim 1, wherein the optical surface is the cornea anterior surface, the lens capsule anterior surface, or the lens capsule posterior surface.

3. The system of claim 2, wherein the control electronics are further programmed:
process returning portions of the sample beam so as to detect third locations on the optical surface beyond the second radial distance and within a third radial distance from the point on the optical surface; and
generate a third surface model of the optical surface based on the location of the point on the optical surface and the first, second, and third locations on the optical surface.

4. The system of claim 1, wherein the control electronics are further programmed to process returning portions of the sample beam so as to detect second locations comprises generating a search volume defined by a first upper limit surface and a first lower limit surface, the first upper and lower limit surfaces being offset from the first surface model on respective opposing sides of the first surface model, and wherein said processing returning portions of the sample beam focused at the plurality of different locations so as to detect second locations is limited to the search volume.

5. The system of claim 1, wherein the control electronics are further programmed:
process returning portions of the sample beam so as to detect third locations on the optical surface beyond the second radial distance and within a third radial distance from the point on the optical surface; and
generate a third surface model of the optical surface based on the location of the point on the optical surface and the first, second, and third locations on the optical surface.

6. The system of claim 1, wherein at least one of the first and second surface models is an ellipsoid surface model, a spherical surface model, or a conicoid surface model.

7. The system of claim 1, wherein a boundary surface within the detection window divides the detection window into a real portion of the detection window and an imaginary portion of the detection window, the detection window imaginary portion being disposed between the laser eye surgery system and the detection window real portion.

8. The system of claim 7, wherein:
the optical surface is the lens capsule anterior surface; and
the reference path length is set to position the lens capsule anterior surface between the detection window boundary surface and the laser eye surgery system.

9. The system of claim 7, wherein:
the optical surface is the lens capsule posterior surface; and
the reference path length is set to position the lens capsule posterior surface between the detection window boundary surface and the laser eye surgery system.

10. The system of claim 1, wherein the control electronics are further programmed:
calculate a transverse distance between an apex of the optical surface and a central axis of the laser eye surgery system;
compare the calculated transverse distance to a predetermined acceptable transverse distance value; and
inhibit treatment of the eye if the calculated transverse distance exceeds the predetermined acceptable transverse distance value.

* * * * *